(12) United States Patent
Cho et al.

(10) Patent No.: US 7,251,514 B2
(45) Date of Patent: *Jul. 31, 2007

(54) BLOOD SUGAR LEVEL MEASURING APPARATUS

(75) Inventors: Ok-Kyung Cho, Schwerte (DE); Yoon-Ok Kim, Schwerte (DE); Katsumi Ouchi, Higashimurayama (JP); Hiroshi Mitsumaki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 590 days.

This patent is subject to a terminal disclaimer.

(21) Appl. No.: 10/812,897

(22) Filed: Mar. 31, 2004

(65) Prior Publication Data

US 2005/0192491 A1 Sep. 1, 2005

(30) Foreign Application Priority Data

Feb. 26, 2004 (JP) ............................. 2004-052072

(51) Int. Cl.
*A61B 5/00* (2006.01)
(52) U.S. Cl. ........................ 600/316; 600/365; 600/326
(58) Field of Classification Search ................ 600/310, 600/316, 322, 323, 326, 365, 549
See application file for complete search history.

(56) References Cited

U.S. PATENT DOCUMENTS

| | | |
|---|---|---|
| 4,306,569 A | 12/1981 | Weil |
| 4,333,803 A | 6/1982 | Seger |
| 4,509,531 A | 4/1985 | Ward |
| 4,750,140 A | 6/1988 | Asano |
| 4,802,489 A | 2/1989 | Nitzan |
| 5,551,422 A | 9/1996 | Simonsen |
| 5,676,143 A | 10/1997 | Simonsen |
| 5,725,480 A | 3/1998 | Oosta |
| 5,732,711 A | 3/1998 | Fitzpatrick |
| 5,743,262 A | 4/1998 | Lepper, Jr. |
| 5,769,784 A | 6/1998 | Barnett |
| 5,795,305 A | 8/1998 | Cho et al. ............. 600/549 |
| 5,924,996 A | 7/1999 | Cho et al. ............. 600/549 |
| 6,226,089 B1 | 5/2001 | Hakamata |
| 6,240,306 B1 | 5/2001 | Rohrscheib |
| 6,269,314 B1 | 7/2001 | Iitawaki et al. |
| 6,280,381 B1 | 8/2001 | Malin |

(Continued)

FOREIGN PATENT DOCUMENTS

EP 0 778 000 A1 6/1997

(Continued)

OTHER PUBLICATIONS

A.R. Scott, "Diabetes Mellitus and Thermoregulation", Can. J. Physiol. Pharmacol, vol. 65, 1987, pp. 1365-1376.

(Continued)

*Primary Examiner*—Eric F Winakur
(74) *Attorney, Agent, or Firm*—Antonelli, Terry, Stout & Kraus, LLP.

(57) ABSTRACT

Blood sugar levels are measured non-invasively based on temperature measurement. Non-invasively measured blood sugar level values obtained by a temperature measurement scheme are corrected by blood oxygen saturation and blood flow volume, thereby stabilizing the measurement data. If the measured blood sugar level is larger than a warning value, a warning is issued.

10 Claims, 19 Drawing Sheets

U.S. PATENT DOCUMENTS

| | | |
|---|---|---|
| 6,353,226 B1 | 3/2002 | Khalil |
| 6,615,061 B1 | 9/2003 | Khalil |
| 2002/0016534 A1 | 2/2002 | Trepagnier et al. |
| 2002/0183646 A1 | 12/2002 | Stivoric et al. |
| 2003/0125612 A1 | 7/2003 | Fox et al. |
| 2003/0152133 A1 | 8/2003 | Ellenz |
| 2003/0216628 A1 | 11/2003 | Bortz et al. |

FOREIGN PATENT DOCUMENTS

| | | |
|---|---|---|
| EP | 1 369 688 | 12/2003 |
| JP | 06317566 | 11/1994 |
| JP | 7-71945 | 3/1995 |
| JP | 08322821 | 12/1996 |
| JP | 10-33512 | 2/1998 |
| JP | 10-108857 | 4/1998 |
| JP | 11505451 | 5/1999 |
| JP | 11155840 | 6/1999 |
| JP | 11-230901 | 8/1999 |
| JP | 11318872 | 11/1999 |
| JP | 2000074829 | 3/2000 |
| JP | 2000506048 | 5/2000 |
| JP | 2000-258343 | 9/2000 |
| JP | 2002535023 | 10/2002 |
| JP | 2003510556 | 3/2003 |
| WO | 01/28417 | 4/2001 |
| WO | WO 01/28414 | 4/2001 |
| WO | 03/010510 | 2/2003 |

OTHER PUBLICATIONS

R.M. Hillson, 'Facial And Sublingual Temperature Changes Following Intravenous Glucose Injection in Diabetics" Diabete & Metabolisme (Paris) 1982,8, pp. 15-19.

Journal of the Medical Association of Thailand, vol. 69, No. 3, 1986, pp. 153-157 (Abstract).

BLOOD SUGAR LEVEL MEASURING APPARATUS

CLAIM OF PRIORITY

The present application claims priority from Japanese application JP 2004-052072 filed on Feb. 26, 2004, the content of which is hereby incorporated by reference to this application.

RELATED APPLICATIONS

The present application is related to U.S. patent application Ser. Nos. 10/620,689, 10/641,262, 10/649,689, 10/765,148, 10/765,986, 10/767,059 and 10/781,675.

BACKGROUND OF THE INVENTION

1. Field of the Invention

The present invention relates to a non-invasive blood sugar level measuring method and apparatus for measuring glucose concentration in a living body without blood sampling.

2. Background Art

Hilson et al. report facial and sublingual temperature changes in diabetics following intravenous glucose injection (Non-Patent Document 1). Scott et al. discuss the issue of diabetics and thermoregulation (Non-Patent Document 2). Based on such researches, Cho et al. suggests a method and apparatus for determining blood glucose concentration by temperature measurement without requiring the collection of a blood sample (Patent Documents 1 and 2).

Various other attempts have been made to determine glucose concentration without blood sampling. For example, a method has been suggested (Patent Document 3) whereby a measurement site is irradiated with near-infrared light of three wavelengths, and the intensity of transmitted light as well as the temperature of the living body is detected. Then, a representative value of the second-order differentiated values of absorbance is calculated, and the representative value is corrected in accordance with the difference between the living body temperature and a predetermined reference temperature. A blood sugar level corresponding to the thus corrected representative value is then determined. An apparatus is also provided (Patent Document 4) whereby a measurement site is heated or cooled while monitoring the living body temperature. The degree of attenuation of light based on light irradiation is measured at the moment of temperature change so that the glucose concentration responsible for the temperature-dependency of the degree of light attenuation can be measured. Further, an apparatus is reported (Patent Document 5) whereby an output ratio between reference light and the light transmitted by an irradiated sample is taken, and then a glucose concentration is calculated by a linear expression of the logarithm of the output ratio and the living body temperature.

[Non-Patent Document 1] R. M. Hilson and T. D. R. Hockaday, "Facial and sublingual temperature changes following intravenous glucose injection in diabetics," Diabete & Metabolisme, 8, pp. 15-19: 1982

[Non-Patent Document 2] A. R. Scott, T. Bennett, I. A. MacDonald, "Diabetes mellitus and thermoregulation," Can. J. Physiol. Pharmacol., 65, pp. 1365-1376: 1987

[Patent Document 1] U.S. Pat. No. 5,924,996

[Patent Document 2] U.S. Pat. No. 5,795,305

[Patent Document 3] JP Patent Publication (Kokai) No. 2000-258343 A

[Patent Document 4] JP Patent Publication (Kokai) No. 10-33512 A (1998)

[Patent Document 5] JP Patent Publication (Kokai) No. 10-108857 A (1998)

SUMMARY OF THE INVENTION

Glucose (blood sugar) in blood is used for glucose oxidation reaction in cells to produce necessary energy for the maintenance of a living body. In the basal metabolism state, in particular, most of the produced energy is converted into heat energy for the maintenance of body temperature. Thus, it can be expected that there is some relationship between blood glucose concentration and body temperature. However, as is evident from the way sicknesses cause fever, the body temperature also varies due to factors other than blood glucose concentration. While methods have been proposed to determine blood glucose concentration by temperature measurement without blood sampling, they lack sufficient accuracy.

It is the object of the invention to provide a method and apparatus for determining blood glucose concentration with high accuracy based on temperature data of a subject without blood sampling.

Blood sugar is delivered to the cells throughout the human body via the blood vessel system, particularly the capillary blood vessels. In the human body, complex metabolic pathways exist. Glucose oxidation is a reaction in which, fundamentally, blood sugar reacts with oxygen to produce water, carbon dioxide, and energy. Oxygen herein refers to the oxygen delivered to the cells via blood. The amount of oxygen supply is determined by the blood hemoglobin concentration, the hemoglobin oxygen saturation, and the volume of blood flow. On the other hand, the heat produced in the body by glucose oxidation is dissipated from the body by convection, heat radiation, conduction, and so on. On the assumption that the body temperature is determined by the balance between the amount of energy produced in the body by glucose burning, namely heat production, and heat dissipation such as mentioned above, we set up the following model:

(1) The amount of heat production and the amount of heat dissipation are considered equal.

(2) The amount of heat production is a function of the blood glucose concentration and the amount of oxygen supply.

(3) The amount of oxygen supply is determined by blood hemoglobin concentration, blood hemoglobin oxygen saturation, and the volume of blood flow in the capillary blood vessels.

(4) The amount of heat dissipation is mainly determined by heat convection and heat radiation.

The inventors have achieved the present invention after realizing that blood sugar levels can be accurately determined on the basis of the results of measuring the temperature of the body surface and simultaneously measuring parameters relating to blood oxygen concentration and blood flow volume, in accordance with the aforementioned model. The parameters can be measured from a part of the human body, such as the fingertip. Parameters relating to convection and radiation can be determined by carrying out thermal measurements on the fingertip. Parameters relating to blood hemoglobin concentration and blood hemoglobin oxygen saturation can be obtained by spectroscopically measuring blood hemoglobin and determining the ratio of hemoglobin bound with oxygen to hemoglobin not bound with oxygen. With regard to the parameters relating to blood hemoglobin concentration and blood hemoglobin oxygen saturation, measurement accuracy would not be significantly lowered if pre-stored constants are employed rather than taking measurements. The parameter relating to the volume of blood flow can be determined by measuring the amount of heat transfer from the skin.

In one aspect, the invention provides a blood sugar level measuring apparatus comprising:

a heat amount measurement portion for measuring a plurality of temperatures derived from a body surface and obtaining information used for calculating the amount of heat transferred by convection and the amount of heat transferred by radiation, both related to the dissipation of heat from said body surface;

an oxygen level measuring portion for obtaining information about blood oxygen level;

a storage portion for storing a relationship between parameters corresponding to said plurality of temperatures and blood oxygen level and blood sugar levels;

a calculating portion which converts a plurality of measurement values fed from said heat amount measuring portion and said oxygen level measurement portion into said parameters, and computes a blood sugar level by applying said parameters to said relationship stored in said storage portion;

a display portion for displaying the blood sugar level calculated by said calculating portion; and a warning control portion, wherein:

said oxygen level measurement portion includes a blood flow volume measurement portion for obtaining information about blood flow volume, and an optical measurement portion for obtaining hemoglobin concentration and hemoglobin oxygen saturation in blood, wherein said blood flow volume measurement portion includes:

a body-surface contact portion;

an adjacent temperature detector disposed adjacent to said body-surface contact portion;

an indirect temperature detector for detecting the concentration at a position spaced apart from said body-surface contact portion; and a heat conducting member connecting said body-surface contact portion and said indirect temperature detector.

In another aspect, the invention provides a blood sugar level measuring apparatus comprising:

an ambient temperature measuring device for measuring ambient temperature;

a body-surface contact portion to which a body surface is brought into contact;

a radiant heat detector for measuring radiant heat from said body surface;

a heat conducting member disposed in contact with said body-surface contact portion;

an adjacent temperature detector disposed adjacent to said body-surface contact portion;

an indirect temperature detector disposed at a position that is adjacent to said heat conducting member and that is spaced apart from said body-surface contact portion, said indirect temperature detector measuring temperature at the position spaced apart from said body-surface contact portion;

a light source for irradiating said body-surface contact portion light with at least two different wavelengths;

a light detector for detecting reflected light produced as said light is reflected by said body surface;

a converter for converting outputs from said adjacent temperature detector, said indirect temperature detector, said ambient temperature detector, said radiant temperature detector and said light detector, into parameters;

a calculating portion in which a relationship between said parameters and blood sugar levels is stored in advance, and which calculates a blood sugar level by applying said parameters to said relationship;

a display for displaying the blood sugar level outputted from said calculating portion; and a warning control portion, wherein:

said warning control portion causes said display portion to display a warning if the blood sugar level calculated by said calculation portion is larger than a warning blood sugar level.

In yet another aspect, the invention provides a blood sugar level measuring apparatus comprising:

an ambient temperature measuring device for measuring ambient temperature;

a body-surface contact portion to which a body surface is brought into contact;

a radiant heat detector for measuring radiant heat from said body surface;

a heat conducting member disposed in contact with said body-surface contact portion;

an adjacent temperature detector disposed adjacent to said body-surface contact portion;

an indirect temperature detector disposed at a position that is adjacent to said heat conducting member and that is spaced apart from said body-surface contact portion, said indirect temperature detector measuring temperature at the position spaced apart from said body-surface contact portion;

a storage portion where information about blood hemoglobin concentration and blood hemoglobin oxygen saturation is stored;

a converter for converting outputs from said adjacent temperature detector, said indirect temperature detector, said ambient temperature measuring device and said radiant heat detector, into a plurality of parameters;

a calculating portion in which a relationship between said parameters and blood sugar levels is stored, said calculating portion including a processing portion for calculating a blood sugar level by applying said parameters to said relationship;

a display for displaying the blood sugar level outputted from said calculating portion; and a warning control portion, wherein:

said warning control portion causes said display portion to display a warning if the blood sugar level calculated by said calculation portion is larger than a warning blood sugar level.

In accordance with the invention, blood sugar levels can be determined in an non-invasive measurement with the same level of accuracy with that of the conventional invasive methods.

The invention can provide a highly accurate non-invasive blood sugar level measuring apparatus and method.

DESCRIPTION OF THE PREFERRED EMBODIMENTS

The invention will now be described by way of preferred embodiments thereof with reference made to the drawings.

Initially, the above-mentioned model will be described in more specific terms. Regarding the amount of heat dissipation, convective heat transfer, which is one of the main causes of heat dissipation, is related to temperature difference between the ambient (room) temperature and the body-surface temperature. The amount of heat dissipation due to radiation, another main cause of dissipation, is proportional to the fourth power of the body-surface temperature according to the Stefan-Boltzmann law. Thus, it can be seen that the amount of heat dissipation from the human body is related to the room temperature and the body-surface temperature. Another major factor related to the amount of heat production, the oxygen supply volume, is expressed as the product of hemoglobin concentration, hemoglobin oxygen saturation, and blood flow volume.

The hemoglobin concentration can be measured based on the absorbance of light at the wavelength (iso-absorption wavelength) at which the molar absorption coefficient of the oxy-hemoglobin and that of the reduced (deoxy-) hemoglobin are equal. The hemoglobin oxygen saturation can be measured by measuring the absorbance of the iso-absorption wavelength and at least one other wavelength at which the ratio of the molar absorption coefficient of the oxy-hemoglobin to that of the reduced (deoxy-) hemoglobin is known, and then solving simultaneous equations. Thus, the hemoglobin concentration and the hemoglobin oxygen saturation can be obtained by measuring absorbance at at least two wavelengths.

The rest is the blood flow volume, which can be measured by various methods. One example will be described below.

Figure 1:
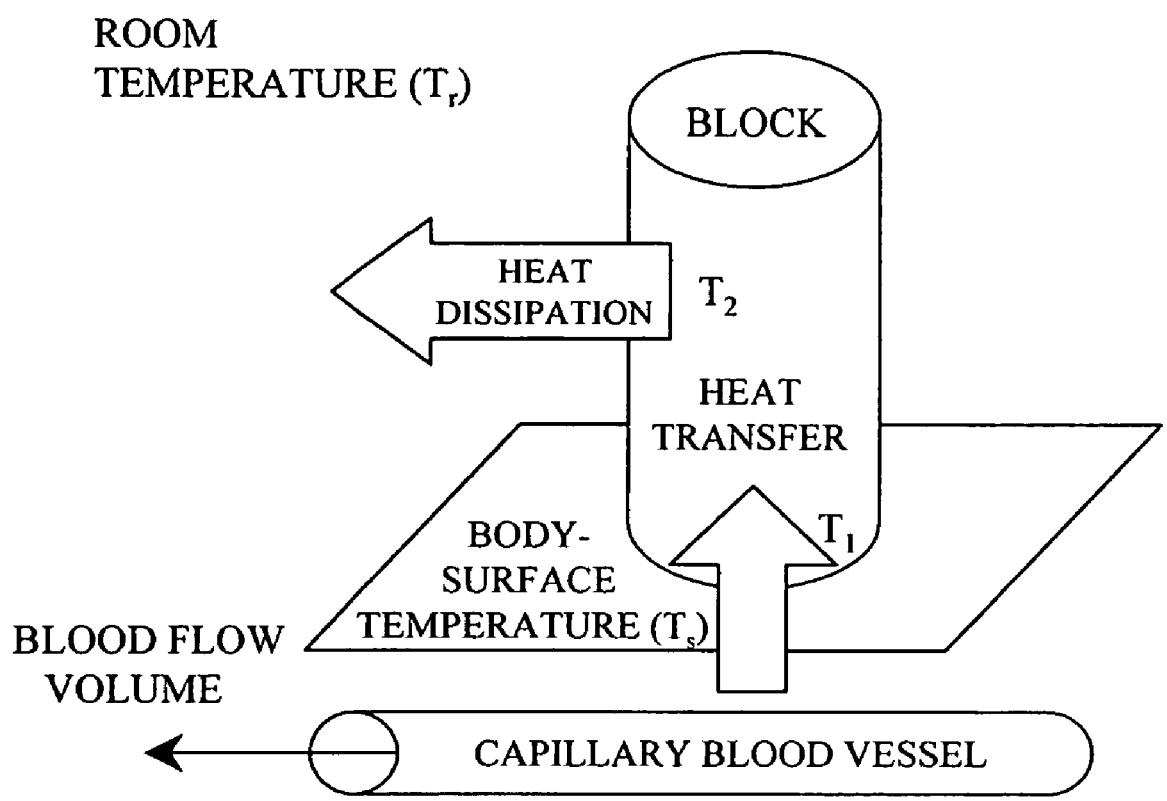
FIG. 1 shows a model of the transfer of heat from a body surface to a block.

FIG. 1 shows a model for the description of the transfer of heat from the body surface to a solid block with a certain heat capacity as the block is brought into contact with the body surface for a certain time and then separated. The block is made of resin such as plastic or vinyl chloride. In the illustrated example, attention will be focused on the chronological variation of a temperature $T_1$ of a portion of the block in contact with the body surface, and the chronological variation of a temperature $T_2$ at a point on the block away from the body surface. The blood flow volume can be estimated by monitoring mainly the chronological variation of the temperature $T_2$ (at the spatially distant point on the block). The details will be described later.

Before the block comes into contact with the body surface, the temperatures $T_1$ and $T_2$ at the two points of the block are equal to the room temperature $T_r$. When a body-surface temperature $T_s$ is higher than the room temperature $T_r$, the temperature $T_1$ swiftly rises as the block comes into contact with the body surface, due to the transfer of heat from the skin, and it approaches the body-surface temperature $T_s$. On the other hand, the temperature $T_2$, which is lower than the temperature $T_1$ due to the dissipation of the heat conducted through the block from its surface, is damped and rises more gradually than the temperature $T_1$. The chronological variation of the temperatures $T_1$ and $T_2$ depends on the amount of heat transferred from the body surface to the block, which in turn depends on the blood flow volume in the capillary blood vessels under the skin. If the capillary blood vessels are regarded as a heat exchanger, the coefficient of heat transfer from the capillary blood vessels to the surrounding cell tissues is given as a function of the blood flow volume. Thus, by measuring the amount of heat transfer from the body surface to the block by monitoring the chronological variation of the temperatures $T_1$ and $T_2$, the amount of heat transmitted from the capillary blood vessels to the cell tissues can be estimated, which in turn makes it possible to estimate the blood flow volume.

Figure 2:
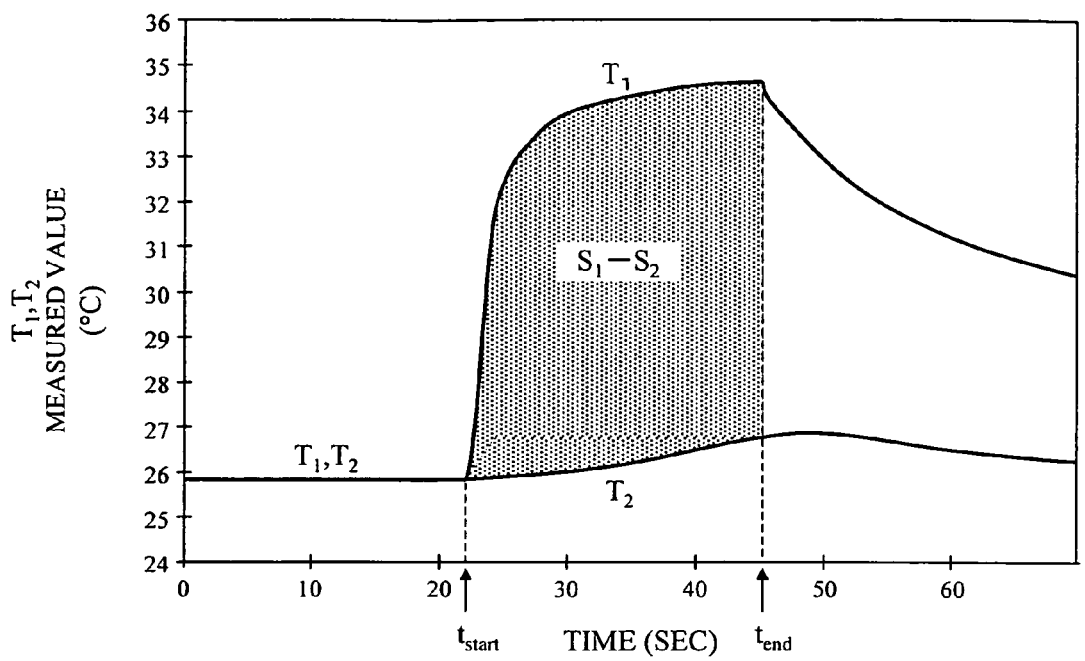
FIG. 2 shows changes in measurement values of temperatures $T_1$ and $T_2$ with time.

FIG. 2 shows the chronological variation of the measured values of the temperature $T_1$ at the portion of the block in contact with the body surface and the temperature $T_2$ at the point on the block away from the body-surface contact position. As the block comes into contact with the body surface, $T_1$ swiftly rises, and it gradually drops as the block is brought out of contact.

Figure 3:
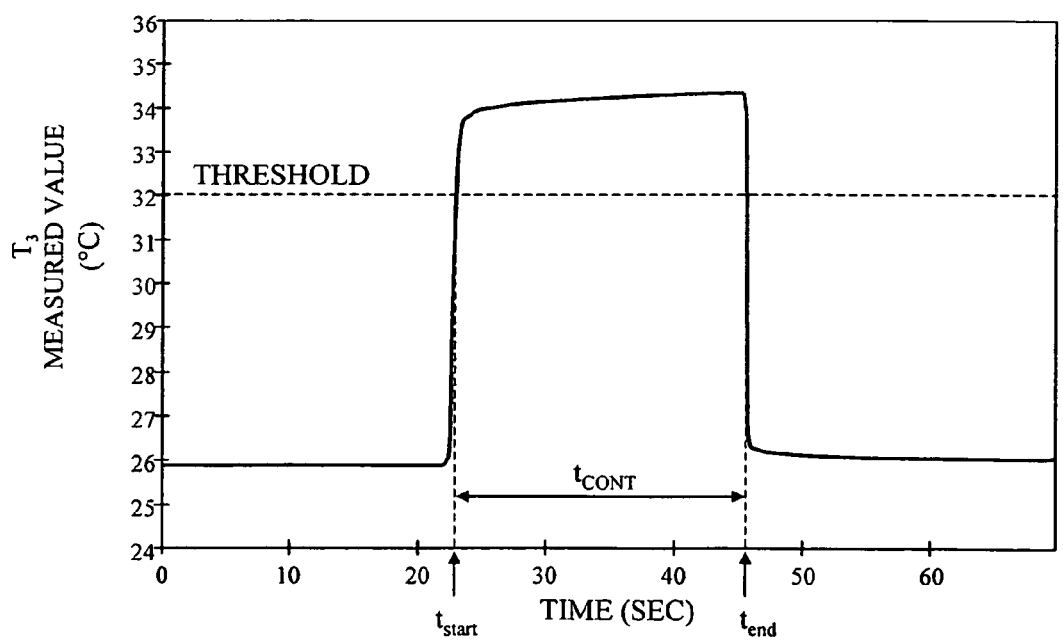
FIG. 3 shows an example of the measurement of a change in temperature $T_3$ with time.

FIG. 3 shows the chronological variation of the measured value of a temperature $T_3$ measured by a radiation temperature detector. As the temperature $T_3$ measured is that due to the radiation from the body surface, this sensor can more sensitively react to temperature changes than other sensors. Because radiation heat propagates as an electromagnetic wave, it can transmit temperature changes instantaneously. Thus, as shown in FIG. 7, which will be described later, by providing the radiation temperature detector near the position where the block is in contact with the body surface in order to detect the radiant heat from the body surface, contact start time $t_{start}$ and contact end time $t_{end}$ of contact between the block and body surface can be detected based on a change in temperature $T_3$. For example, when a temperature threshold value is set as shown in FIG. 3, it can be determined that contact start time $t_{start}$ is when the temperature threshold value is exceeded, and contact end time $t_{end}$ is when the measured temperature drops below the temperature threshold value. The temperature threshold value may be set at 32° C., for example.

Then, the $T_1$ measured value between $t_{start}$ and $t_{end}$ is approximated by an S curve, such as a logistic curve. A logistic curve is expressed by the following equation:

$$T = \frac{b}{1 + c \times \exp(-a \times t)} + d$$

where T is temperature, and t is time.

The measured value can be approximated by determining factors a, b, c, and d by the non-linear least-squares method. For the resultant approximate expression, T is integrated between time $t_{start}$ and time $t_{end}$ to obtain a value $S_1$.

Similarly, an integrated value $S_2$ is calculated from the $T_2$ measured value. The smaller the $(S_1-S_2)$ is, the larger the amount of transfer of heat from the finger surface to the position of $T_2$. $(S_1-S_2)$ becomes larger with increasing finger contact time $t_{cont}(=t_{end}-t_{start})$. Thus, $a_5/(t_{cont} \times (S_1-S_2))$ is designated as a parameter $X_5$ indicating the volume of blood flow, where $a_5$ is a proportionality coefficient.

It will be seen from the above description that the measured quantities necessary for the determination of blood glucose concentration by the aforementioned model are the room temperature (ambient temperature), body surface temperature, temperature changes in the block in contact with the body surface, the temperature due to radiation from the body surface, and the absorbance of at least two wavelengths.

Figure 4:
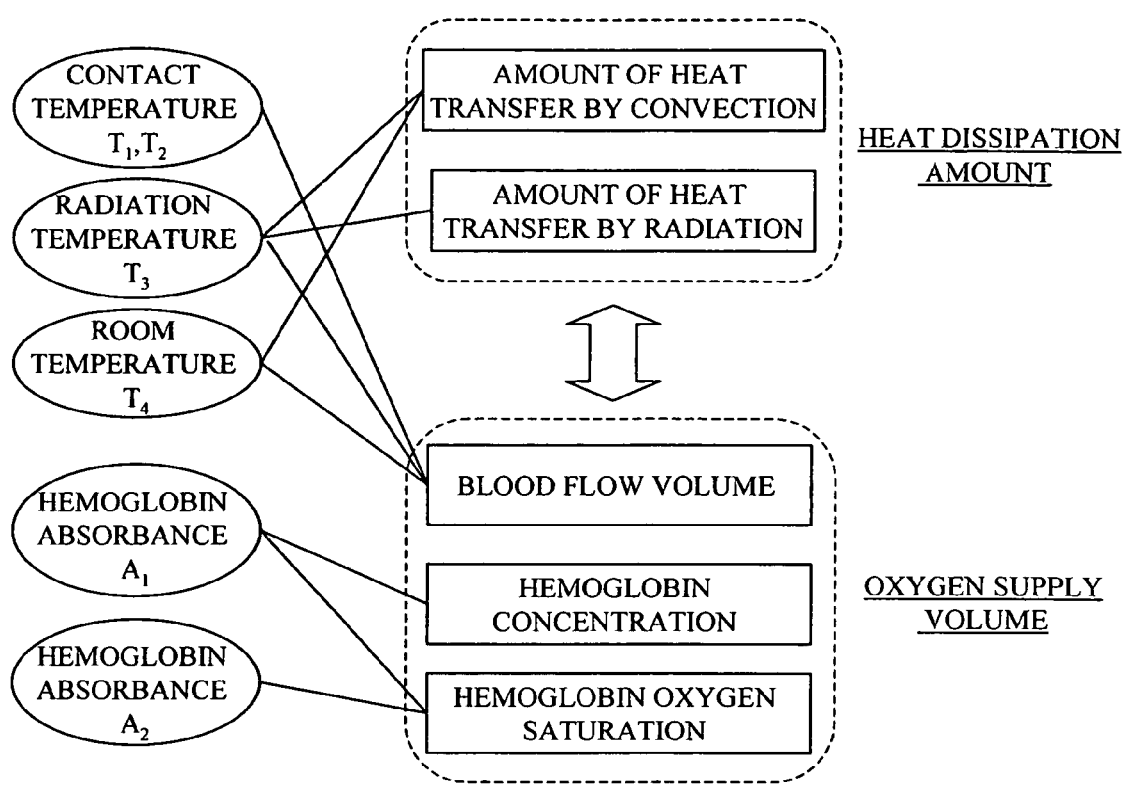
FIG. 4 shows the relationship between measurement values obtained by various sensors and parameters derived therefrom.

FIG. 4 shows the relationships between the measured values provided by various sensors and the parameters derived therefrom. A block is brought into contact with the body surface, and chronological changes in the two kinds of temperatures $T_1$ and $T_2$ are measured by two temperature sensors provided at two locations of the block. Separately, the radiation temperature $T_3$ on the body surface and the room temperature $T_4$ are measured. Absorbance $A_1$ and $A_2$ are measured at at least two wavelengths related to the absorption of hemoglobin. The temperatures $T_1$, $T_2$, $T_3$, and $T_4$ provide parameters related to the volume of blood flow. The temperature $T_3$ provides a parameter related to the amount of heat transferred by radiation. The temperatures $T_3$ and $T_4$ provide parameters related to the amount of heat transferred by convection. Absorbance $A_1$ provides a parameter relating to hemoglobin concentration. Absorbance $A_1$ and $A_2$ provide parameters relating to hemoglobin oxygen saturation.

Hereafter, an example of the apparatus for non-invasively measuring blood sugar levels according to the principle of the invention will be described.

Figure 5:
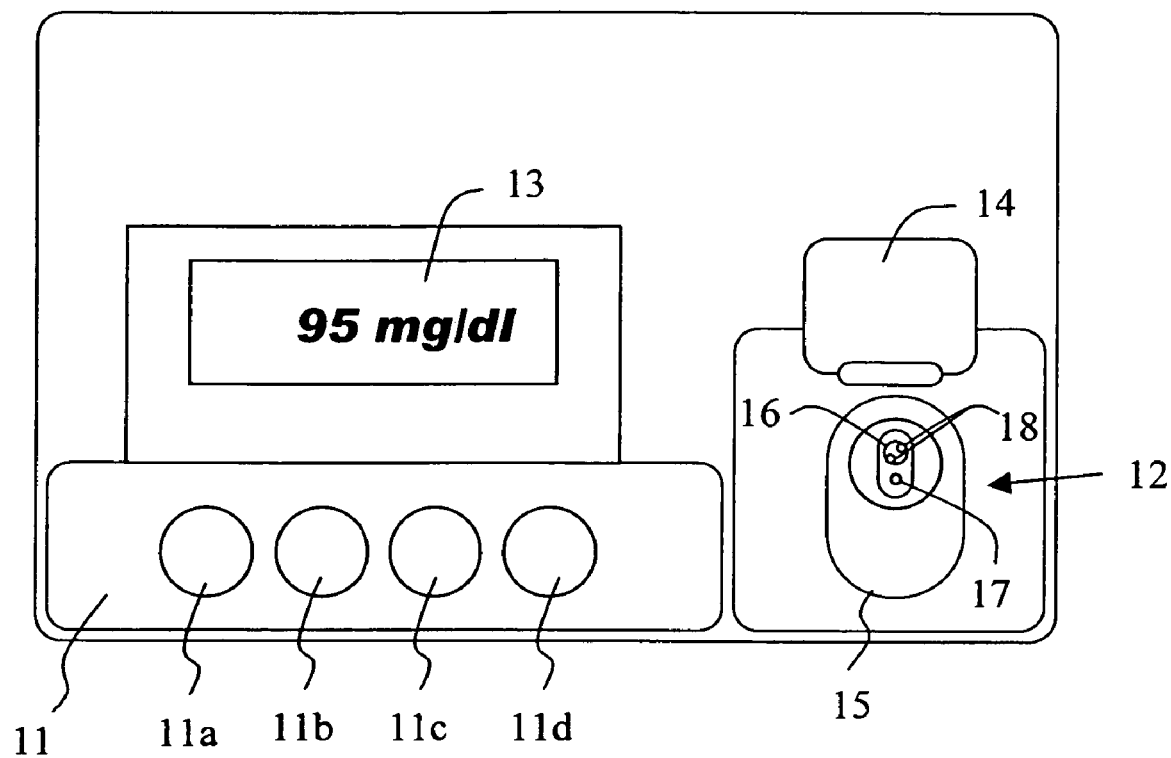
FIG. 5 shows a top plan view of a non-invasive blood sugar level measuring apparatus according to the present invention.

FIG. 5 shows a top plan view of the non-invasive blood sugar level measuring apparatus according to the invention. While in this example the skin on the ball of the fingertip is used as the body surface, other parts of the body surface may be used.

On the upper surface of the apparatus are provided an operating portion 11, a measurement portion 12 where the finger to be measured is to be placed, and a display portion 13 for displaying the result of measurement, the state of the apparatus, measured values, and so on. The operating portion 11 includes four push buttons 11a to 11d for operating the apparatus. The measurement portion 12 has a cover 14 which, when opened (as shown), reveals a finger rest portion 15 with an oval periphery. The finger rest portion 15 accommodates an opening end 16 of a radiation temperature sensor portion, a contact temperature sensor portion 17, and an optical sensor portion 18.

Figure 6:
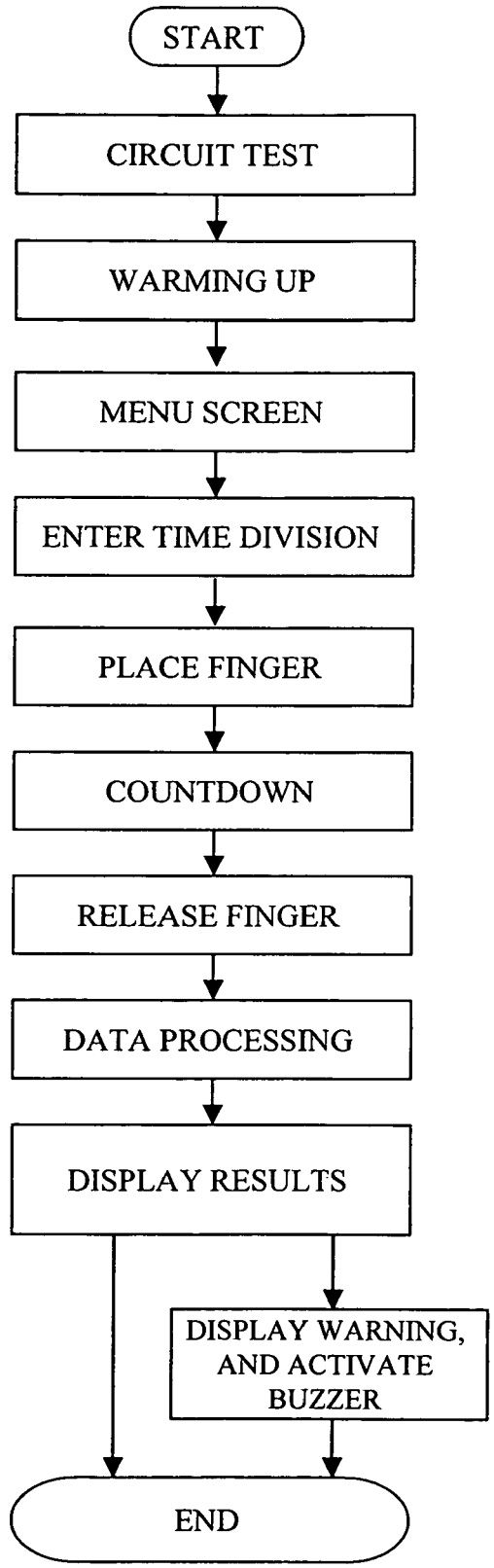
FIG. 6 shows the flow of operation of the apparatus.

FIG. 6 shows the operation procedure for the apparatus. As a button in the operation portion is pressed and the apparatus is turned on, the LCD displays "WARMING UP," during which the electronic circuitry in the apparatus is warmed up. Simultaneously, a check program is activated to automatically check the electronic circuitry. After the end of "WARMING UP," the LCD portion displays a menu screen.

Figure 10:
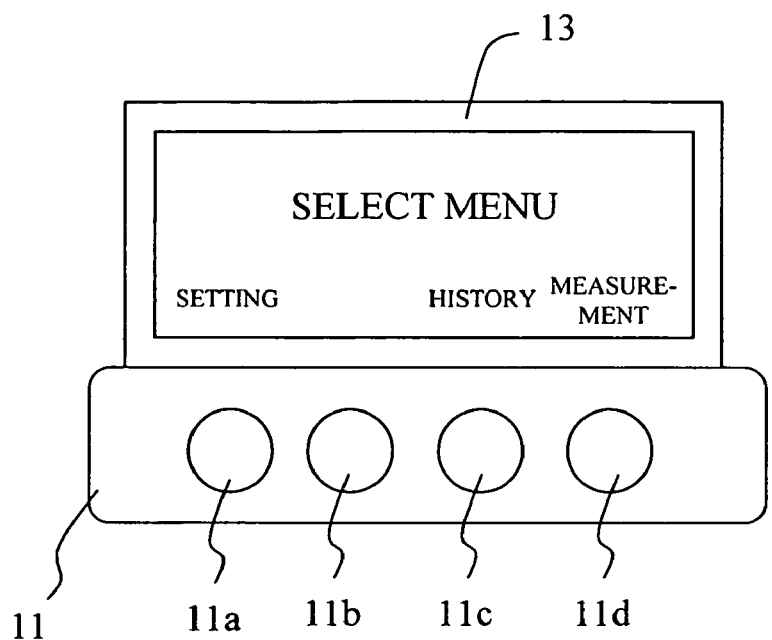
FIG. 10 shows a menu screen.

FIG. 10 shows a menu screen. If the button 11d, 11c, or 11a is pressed, the apparatus enters into a measurement mode, a history mode, or a setting mode, respectively.

Figure 11:
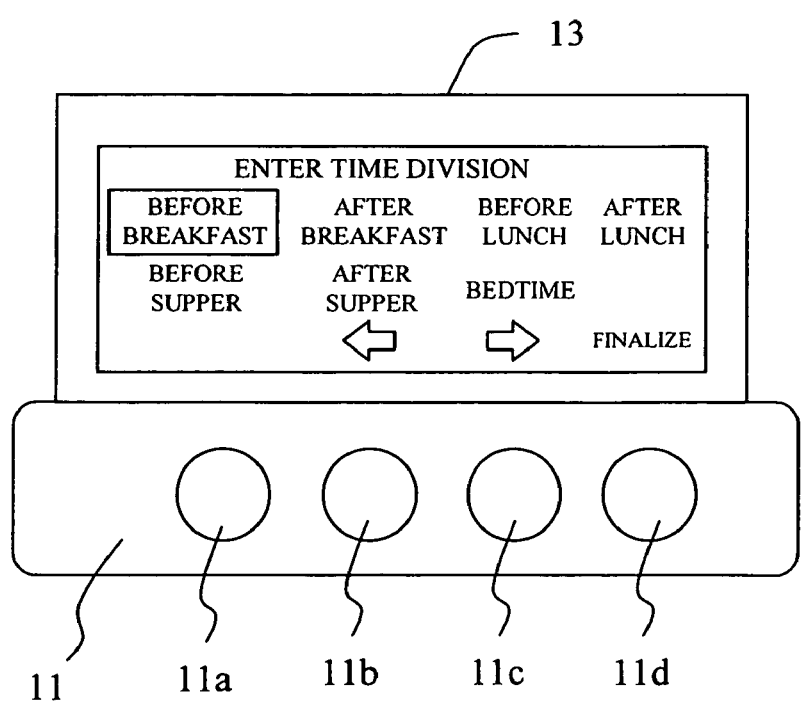
FIG. 11 shows an example of display on an LCD portion.

If the button 11d is pressed to enter into the measurement mode, the LCD portion displays "ENTER TIME DIVISION," as shown in FIG. 11. The subject then presses button 11b or 11c to select one of "BEFORE BREAKFAST," "AFTER BREAKFAST," "BEFORE LUNCH," "AFTER LUNCH," "BEFORE SUPPER," "AFTER SUPPER," AND "BEDTIME," and finalizes the selected time division by pressing the button 11d. After approximately 30 seconds layer, the LCD portion displays "PLACE FINGER." As the subject places his or her finger on the finger rest portion, the LCD portion displays a countdown. After the end of countdown, the LCD portion displays "RELEASE FINGER." As the subject releases his or her finger from the finger rest portion, the LCD portion displays "DATA PROCESSING" and then the blood sugar level that has been calculated.

If (1) the calculated blood sugar level is below 70 mg/dL, the LCD portion displays a warning message in order to warn the subject that he or she is in a state of hypoglycemia, with a beep of a buzzer. The LCD also displays a warning statement and activate the buzzer in the following cases: (2) the time division is before meal and the calculated blood sugar level is above 126 mg/dL; (3) the time division is after meal and the calculated blood sugar level is above 200 nm/dL; (4) the time division is before meal and the calculated blood sugar level is above a before-meal warning value that has been set by the subject; (5) the time division is after meal and the calculated blood sugar level is above a bedtime warning value that has been set by the subject; and (6) the time division is bedtime and the calculated blood sugar level is more than a bedtime warning value set by the subject. Thereafter, the displayed blood sugar level is stored in an IC card, together with the date of measurement and the time division. The subject then reads the displayed blood sugar level and presses the button 11d in the operation portion to return to the menu screen.

Figure 12:
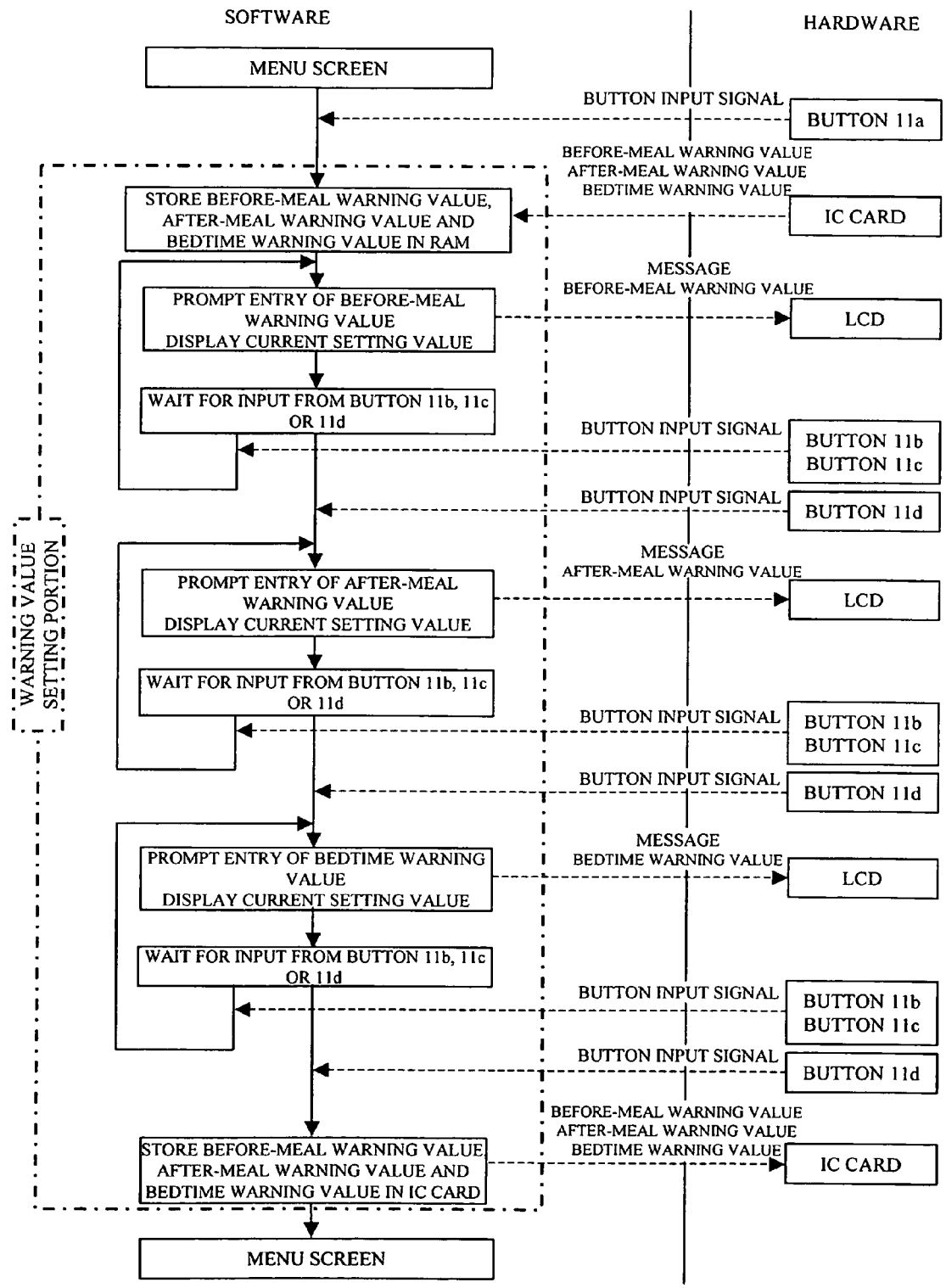
FIG. 12 shows the flow of operation of a warning value setting portion.

FIG. 12 shows the flow of operation of a warning-value setting portion in terms of software. As the subject presses the button 11a on the menu screen shown in FIG. 10, the software reads the before-meal warning value, after-meal warning value, and bedtime warning value from the IC card that have been previously set, and then stores them in the RAM. The software then causes a message "ENTER BEFORE-MEAL WARNING VALUE" to appear on the LCD, on which the previously set before-meal warning value is displayed. The value can be increased by pressing button 11c, and decreased by pressing button 11b. The subject thus adjusts the before-meal warning value by means of the buttons 11b and 11c, and then finalizes the before-meal warning value by pressing button 11d and proceeds to the screen for setting the after-meal warning value. In a similar manner, the after-meal warning value and the bedtime warning value are set, and then the software writes the finalized before-meal warning value, after-meal warning value and bedtime warning value into the IC card. After the writing into the IC card is completed, the software returns to the menu screen.

Figure 13:
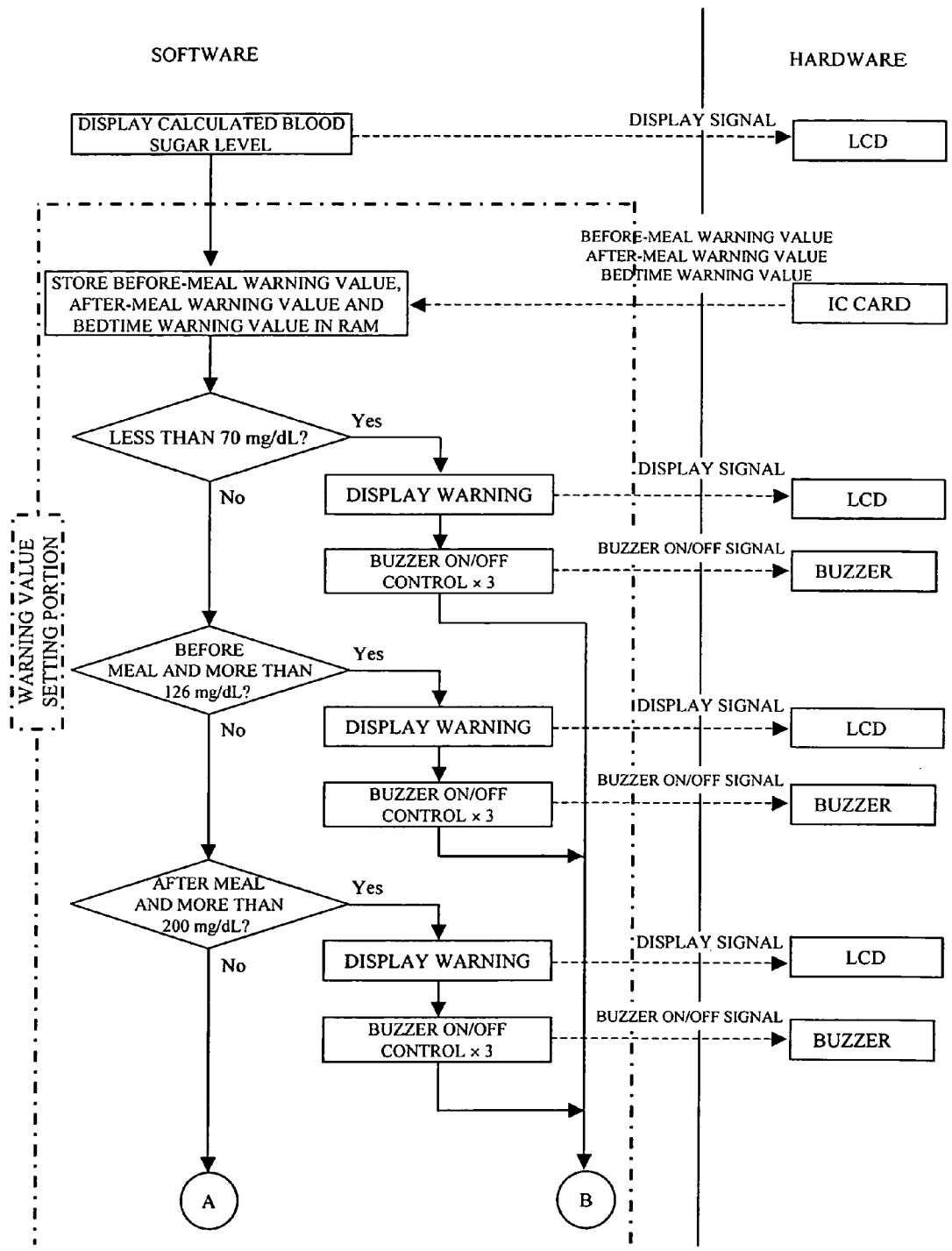
FIG. 13 shows the flow of operation of a warning control portion.
Figure 14:
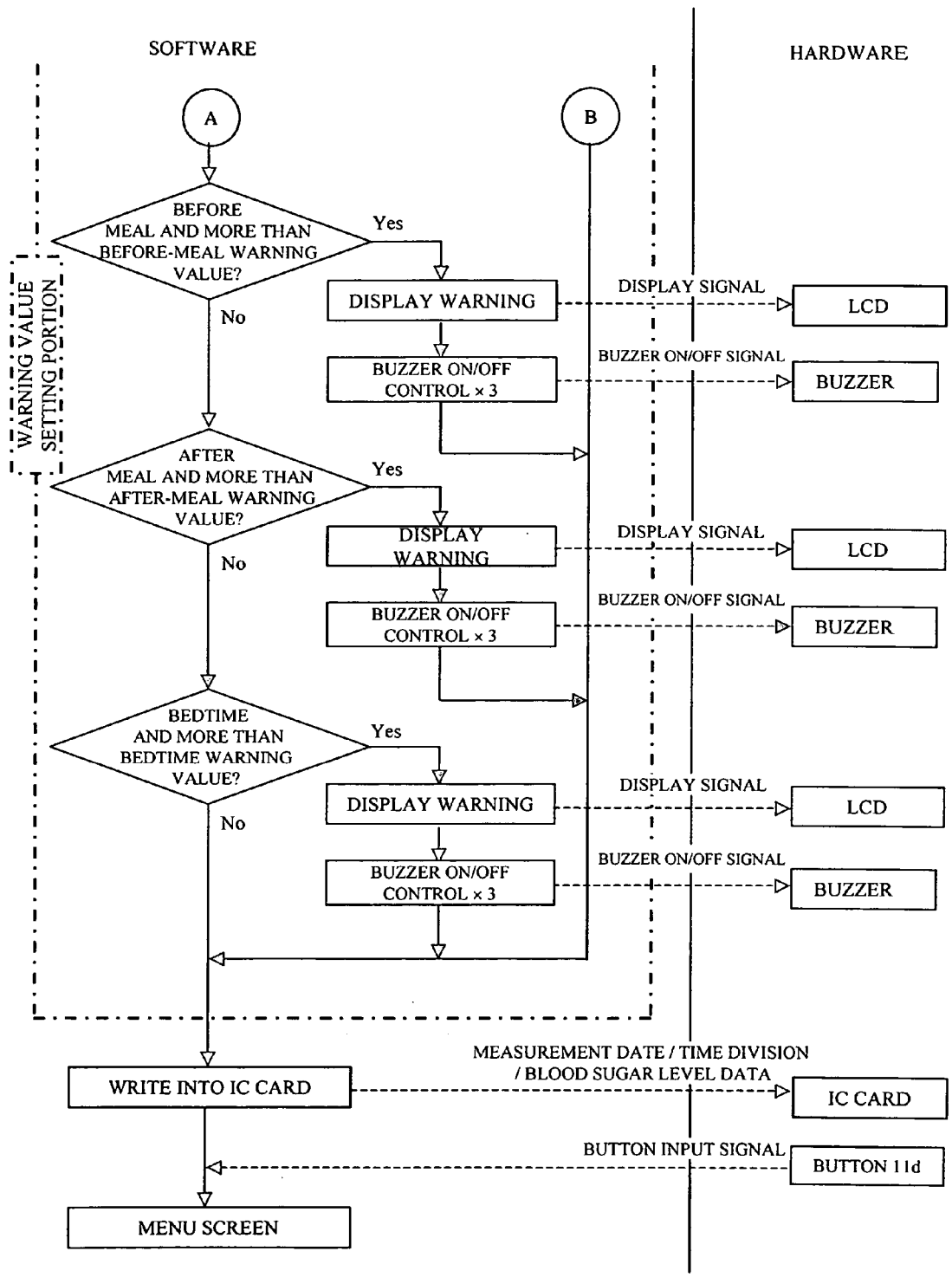
FIG. 14 shows the flow of operation of a warning control portion.
Figure 15:
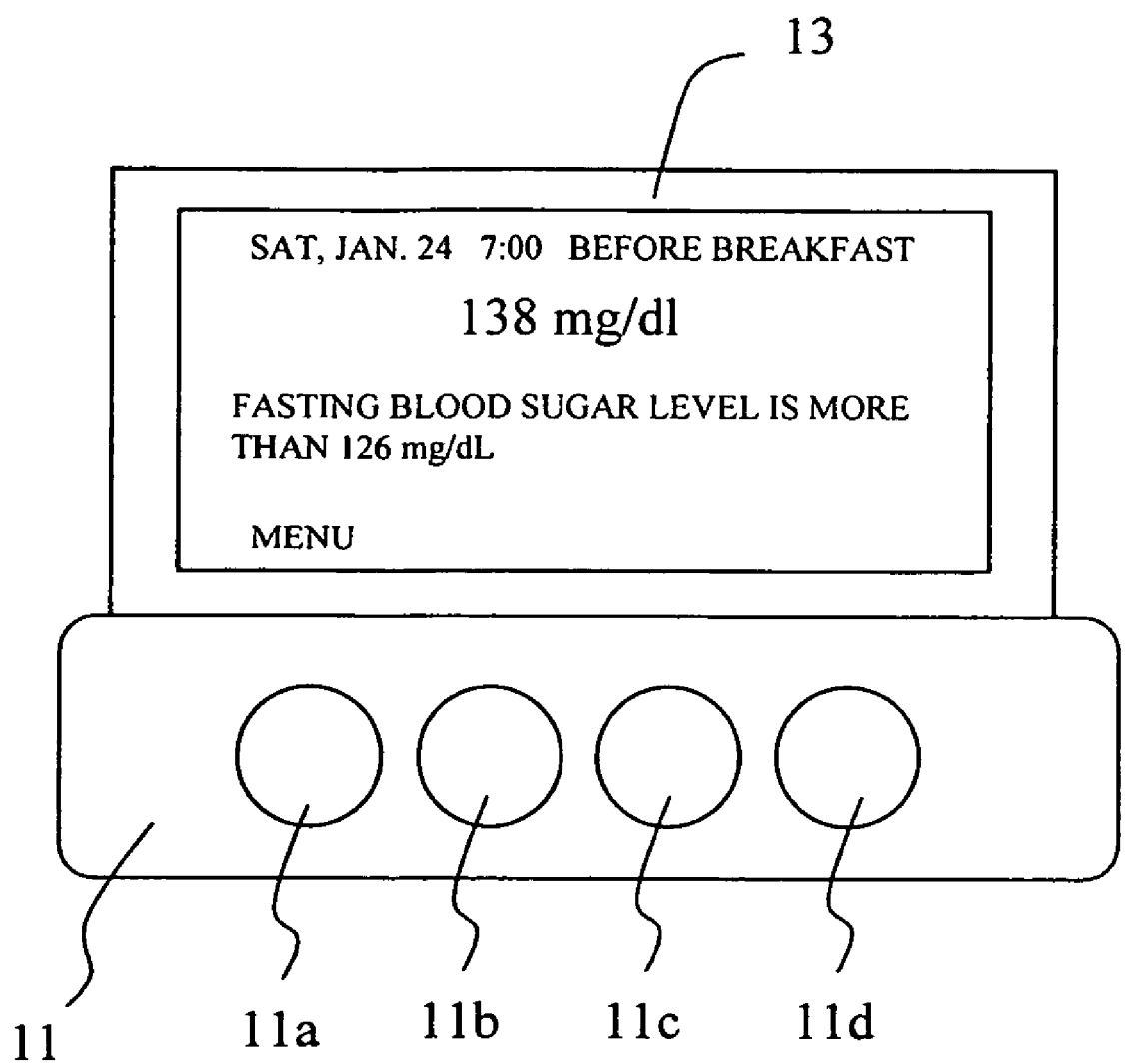
FIG. 15 shows an example of display on an LCD portion.

FIGS. 13 and 14 show the flow of operation of a warning control portion in terms of software. After the blood sugar level is calculated, the software reads the before-meal blood sugar level, before-meal warning value, and before-breakfast warning value from the IC card and then stores them in RAM. If the calculated blood sugar level is below 70 mg/dL, the software displays "Blood sugar level is below 70 mg/dL" on the LCD along with the calculated blood sugar level that is already displayed, and repeats an ON/OFF control of the buzzer three times. If the time division is before meal, namely if it is either before breakfast, before lunch, or before supper, and if the calculated blood sugar level is more than 126 mg/dL, the software displays a warning message "Fasting blood sugar level is over 126 mg/dL" on the LCD along with the calculated blood sugar level that is displayed, and repeats the ON/OFF control of the buzzer three times. FIG. 15 shows how this is displayed on the LCD. If the time division is after meal, namely if it is either after breakfast, after lunch, or after supper, and if the calculated blood sugar level is over 200 mg/dL, the software displays a warning message "Nonfasting blood sugar level is over 200 mg/dL" on the LCD along with the calculated blood sugar level that is already displayed, and repeats the ON/OFF control of the buzzer three times.

If none of the above conditions is met, the software compares the calculated blood sugar level with the warning value set by the subject. First, if the time division is before meal, namely either before breakfast, before lunch, or before supper, and if the calculated blood sugar level exceeds the before-meal warning value, the software displays a warning message "Fasting blood sugar level is over XXX mg/dL" on the LCD along with the calculated blood sugar level that is already displayed, and repeats the ON/OFF control of the buzzer three times. In the space XXX, there is entered the before-meal warning value. If the time division is after meal, namely either after breakfast, after lunch, or after supper, and if the calculated blood sugar level exceeds the after-meal warning value, the software displays a warning message "Nonfasting blood sugar level is over YYY mg/dL" on the LCD, along with the calculated blood sugar level that is already displayed, and repeats the ON/OFF control of the buzzer three times. In the space YYY, there is entered the after-meal warning value. If the time division is bedtime and if the calculated blood sugar level is more than the bedtime warning value, the software displays a warning message "Bedtime blood sugar level is over ZZZ mg/dL" on the LCD along with the calculated blood sugar level that is already displayed, and repeats the ON/OFF control three times. In the space ZZZ, there is entered the bedtime warning value. After leaving the warning control portion, the software writes measurement data consisting of the date of measurement, time division, and blood sugar level data, into the IC card.

Figure 16:
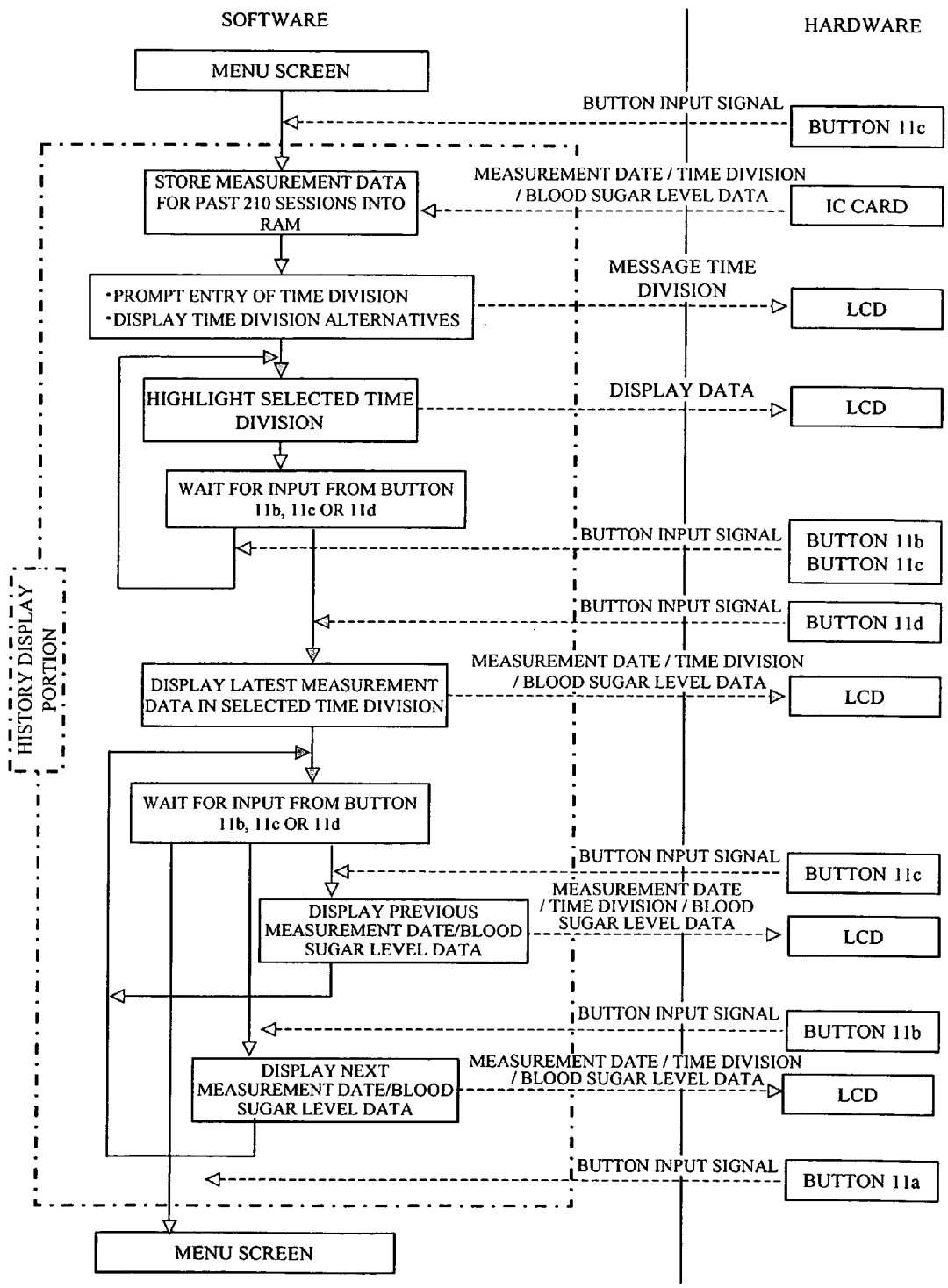
FIG. 16 shows the flow of operation of a history display portion.
Figure 17:
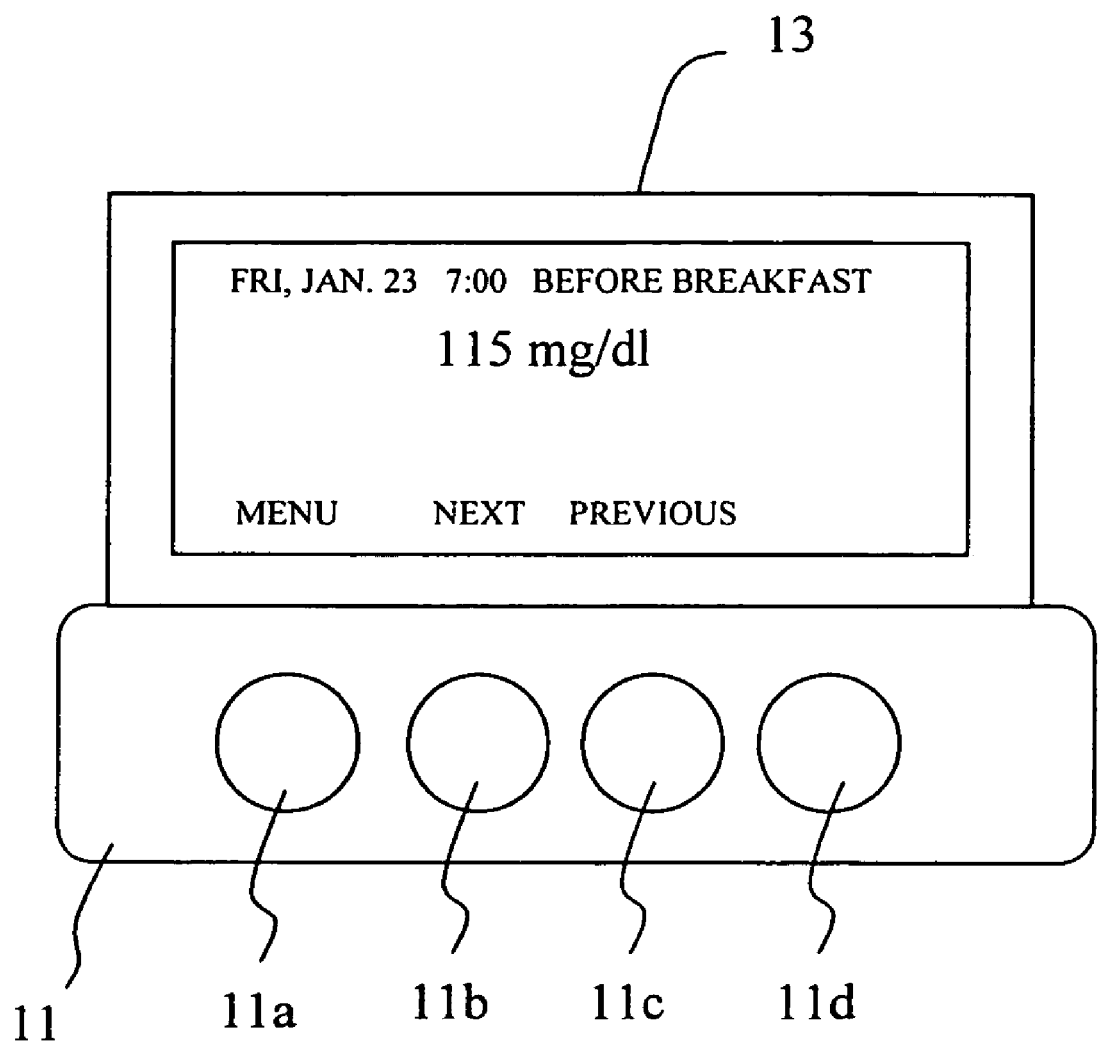
FIG. 17 shows an example of history data.

FIG. 16 shows the flow of operation of a history display portion. In the menu screen of FIG. 10, as the subject presses button 11c, the software reads from the IC card the measurement data including the date of measurement, time division and blood sugar level data for the past 210 sessions, and stores the data in RAM. The software then displays a message "Enter time division" on the LCD portion, as shown in FIG. 11. The subject presses button 11b or 11c to select one of "BEFORE BREAKFAST," "AFTER BREAKFAST," "BEFORE LUNCH," "AFTER LUHCN," "BEFORE SUPPER," "AFTER SUPPER," AND "BEDTIME" and finalizes the selected time division by pressing button 11d. Thereafter, the software displays the latest measurement data of the selected time division on the LCD, and then waits for the input via button 11a, 11b or 11c from the subject. If the button 11c is pressed, the software displays previous measurement data in the same time division. If the button 11b is pressed, the software displays subsequent measurement data in the same time division. If the button 11a is pressed, the software returns to the menu screen. FIG. 17 shows an example of the history data displayed on the LCD. The history data on a time-division basis thus provides useful targets when the subject intends to control the amount of insulin dosage and the amount of meal for breakfast, lunch, and supper.

Figure 18:
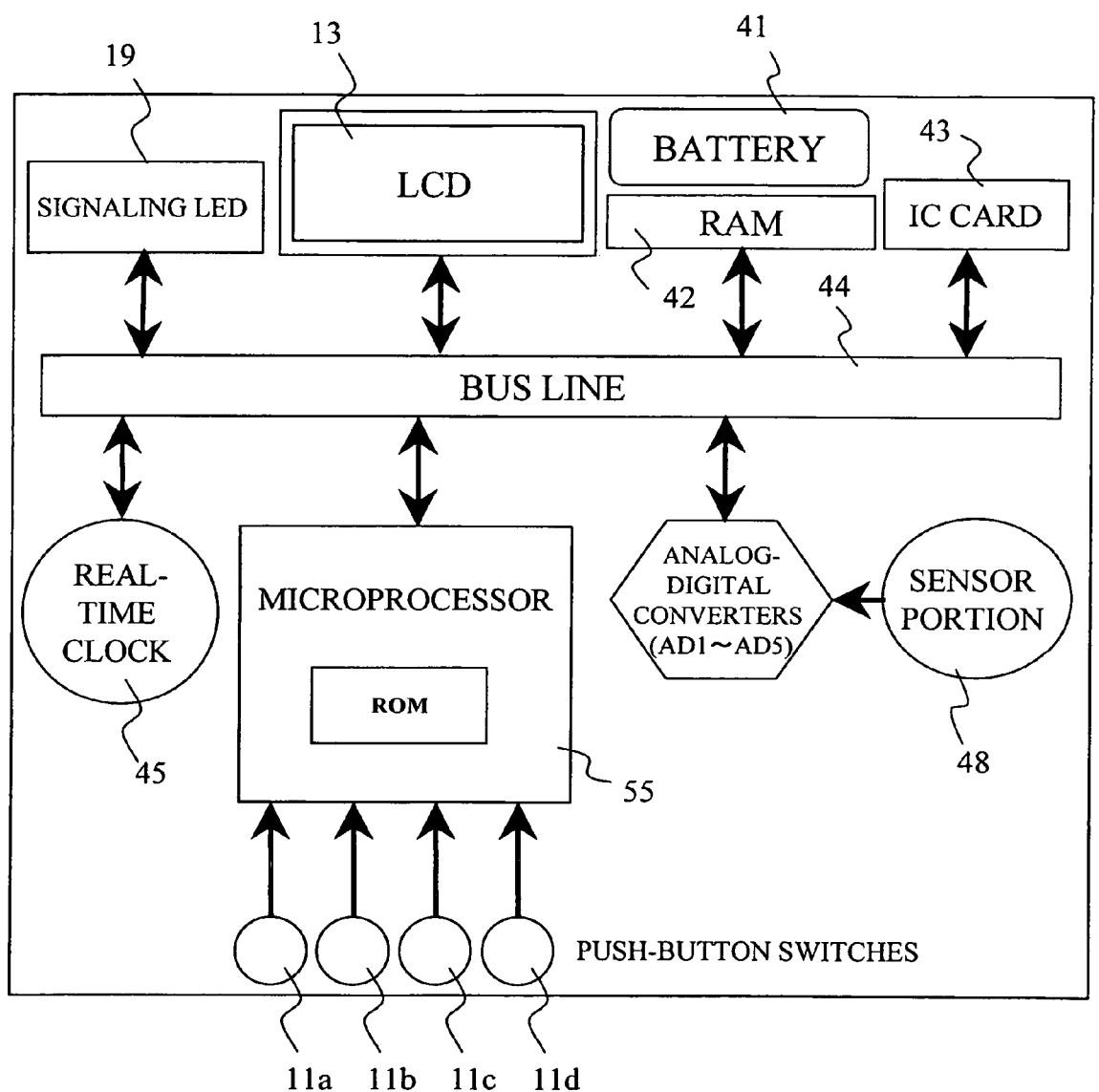
FIG. 18 shows a functional block diagram of the apparatus.

FIG. 18 shows a functional block diagram of the apparatus according to the embodiment. The apparatus runs on battery 41. Signals measured by sensor portion 48 including temperature and optical sensors is fed to analog/digital converters AD1 to AD5 provided for individual signals and is converted into digital signals. A microprocessor 55 has built inside a ROM for storing software. An LED selecting LSI 19, under the control of microprocessor 55, is adapted to cause two light-emitting diodes, which are the light source of the optical sensor, to emit light in a time-divided manner. Peripheral circuits to microprocessor 55 include analog-digital converters AD1 to AD5, LCD 13, LED-selecting LSI 19, RAM 42, IC card 43, and realtime clock 45. Microprocessor 55 can access any of these via bus line 44. Push buttons 11a to 11d are connected to microprocessor 55. A buzzer 56 is also connected to microprocessor 55. The buzzer 56 can be turned on or off by microprocessor 55.

Figure 7A:
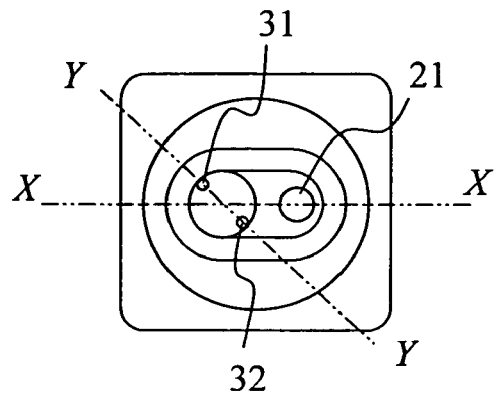
FIG. 7 shows the details of a measurement portion.
Figure 7B:
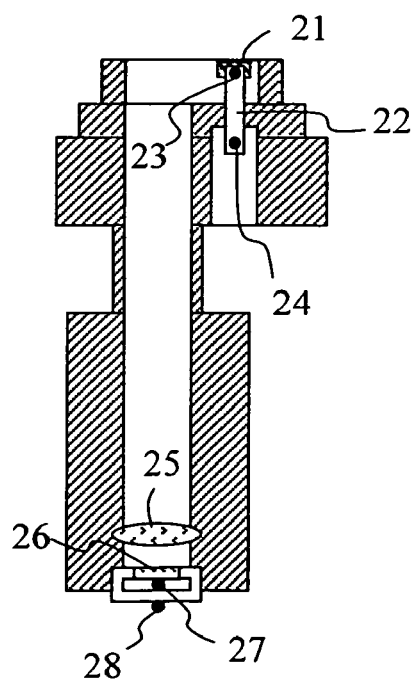

FIG. 7 shows the details of the measurement portion. FIG. 7(a) is a top plan view, (b) is a cross section taken along line XX of (a), and (c) is a cross section taken along YY of (a).

First, temperature measurement by the non-invasive blood sugar level measuring apparatus according to the invention will be described. A thin plate 21 of a highly heat-conductive material, such as gold, is disposed on a portion where a measured portion (ball of the finger) is to come into contact. A bar-shaped heat-conductive member 22 made of a material with a heat conductivity lower than that of the plate 21, such as polyvinylchloride, is thermally connected to the plate 21 and extends into the apparatus. The temperature sensors include a thermistor 23, which is an adjacent temperature detector with respect to the measured portion for measuring the temperature of the plate 21. There is also a thermistor 24, which is an indirect temperature detector with respect to the measured portion for measuring the temperature of a portion of the heat-conducting member away from the plate 21 by a certain distance. An infrared lens 25 is disposed inside the apparatus at such a position that the measured portion (ball of the finger) placed on the finger rest portion 15 can be seen through the lens. Below the infrared lens 25, there is disposed a pyroelectric detector 27 via an infrared radiation-transmitting window 26. Another thermistor 28 is disposed near the pyroelectric detector 27.

Figure 7C:
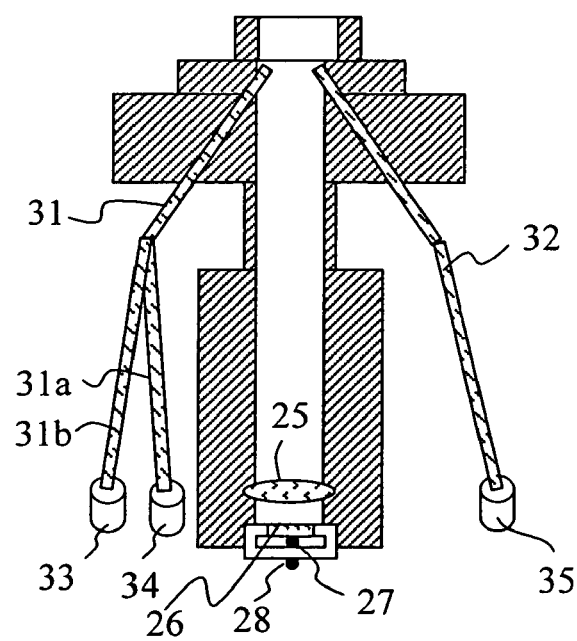

Thus, the temperature sensor portion of the measurement portion has four temperature sensors, and they measure four kinds of temperatures as follows:

(1) Temperature on the finger surface (thermistor 23): $T_1$
(2) Temperature of the heat-conducting member (thermistor 24): $T_2$
(3) Temperature of radiation from the finger (pyroelectric detector 27): $T_3$
(4) Room temperature (thermistor 28): $T_4$ The optical sensor portion 18 will be described. The optical sensor portion measures the hemoglobin concentration and hemoglobin oxygen saturation for obtaining the oxygen supply volume. For measuring the hemoglobin concentration and hemoglobin oxygen saturation, absorbance must be measured at at least two wavelengths. FIG. 7(c) shows an example of an arrangement for performing the two-wavelength measurement using two light sources 33 and 34 and one detector 35.

Inside the optical sensor portion 18, there are disposed the end portions of two optical fibers 31 and 32. The optical fiber 31 is for irradiating light, and the optical fiber 32 is for receiving light. As shown in FIG. 7(c), the optical fiber 31 is connected to branch fibers 31a and 31b at the ends of which light-emitting diodes 33 and 34 with two different wavelengths are provided. At the end of the optical fiber 32, there is provided a photodiode 35. The light-emitting diode 33 emits light of a wavelength 810 nm. The light-emitting diode 34 emits light of a wavelength 950 nm. The wavelength 810 nm is the iso-absorption wavelength at which the molar absorption coefficients of oxy-hemoglobin and reduced (deoxy-) hemoglobin are equal. The wavelength 950 nm is the wavelength at which the difference in molar absorption coefficients between the oxy-hemoglobin and the reduced hemoglobin is large.

The two light-emitting diodes 33 and 34 emit light in a time-divided manner. The light emitted by the light-emitting diodes 33 and 34 is irradiated via the light-emitting optical fiber 31 onto the finger of the subject. The light with which the finger is irradiated is reflected by the finger skin, incident on the light-receiving optical fiber 32, and then detected by the photodiode 35. When the light with which the finger is irradiated is reflected by the finger skin, some of the light penetrates through the skin and into the tissue, and is then absorbed by the hemoglobin in the blood flowing in capillary blood vessels. The measurement data obtained by the photodiode 35 is reflectance R, and the absorbance is approximated by log (1/R). Irradiation is conducted with light of the wavelengths 810 nm and 950 nm, and R is measured for each, and then log (1/R) is calculated, thereby measuring absorbance $A_1$ for wavelength 810 nm and absorbance $A_2$ for wavelength 950 nm.

When the reduced hemoglobin concentration is [Hb], and the oxy-hemoglobin concentration is [HbO$_2$], absorbance $A_1$ and $A_2$ are expressed by the following equations:

$$A_1 = a \times ([Hb] \times A_{Hb}(810 \text{ nm}) + [HbO_2] \times A_{HbO_2}(810 \text{ nm}))$$
$$= a \times ([Hb] + [HbO_2]) \times A_{HbO_2}(810 \text{ nm})$$
$$A_2 = a \times ([Hb] \times A_{Hb}(950 \text{ nm}) + [HbO_2] \times A_{HbO_2}(950 \text{ nm}))$$
$$= a \times ([Hb] + [HbO_2]) \times \left(\left(1 - \frac{[HbO_2]}{[Hb] + [HbO_2]}\right) \times A_{Hb}(950 \text{ nm}) + \frac{[HbO_2]}{[Hb] + [HbO_2]} \times A_{HbO_2}(950 \text{ nm})\right)$$

$A_{Hb}$ (810 nm) and $A_{Hb}$ (950 nm), and $A_{HbO2}$ (810 nm) and $A_{HbO2}$ (950 nm) are molar absorption coefficients of reduced hemoglobin and oxy-hemoglobin, respectively, and are known at the respective wavelengths. Sign a is a proportional coefficient. Based on the above equations, the hemoglobin concentration ([Hb]+[HbO$_2$]) and the hemoglobin oxygen saturation {[HbO$_2$]/([Hb]+[HbO$_2$])} can be determined as follows:

$$[Hb] + [HbO_2] = \frac{A_1}{a \times A_{HbO_2}(810 \text{ nm})}$$

$$\frac{[HbO_2]}{[Hb] + [HbO_2]} = \frac{A_2 \times A_{HbO_2}(810 \text{ nm}) - A_1 \times A_{Hb}(950 \text{ nm})}{A_1 \times (A_{HbO_2}(950 \text{ nm}) - A_{Hb}(950 \text{ nm}))}$$

While in the above example the hemoglobin concentration and hemoglobin oxygen saturation are measured by measuring absorbance at two wavelengths, it is possible to reduce the influence of interfering components and increase measurement accuracy by measuring at three or more wavelengths.

Figure 8:
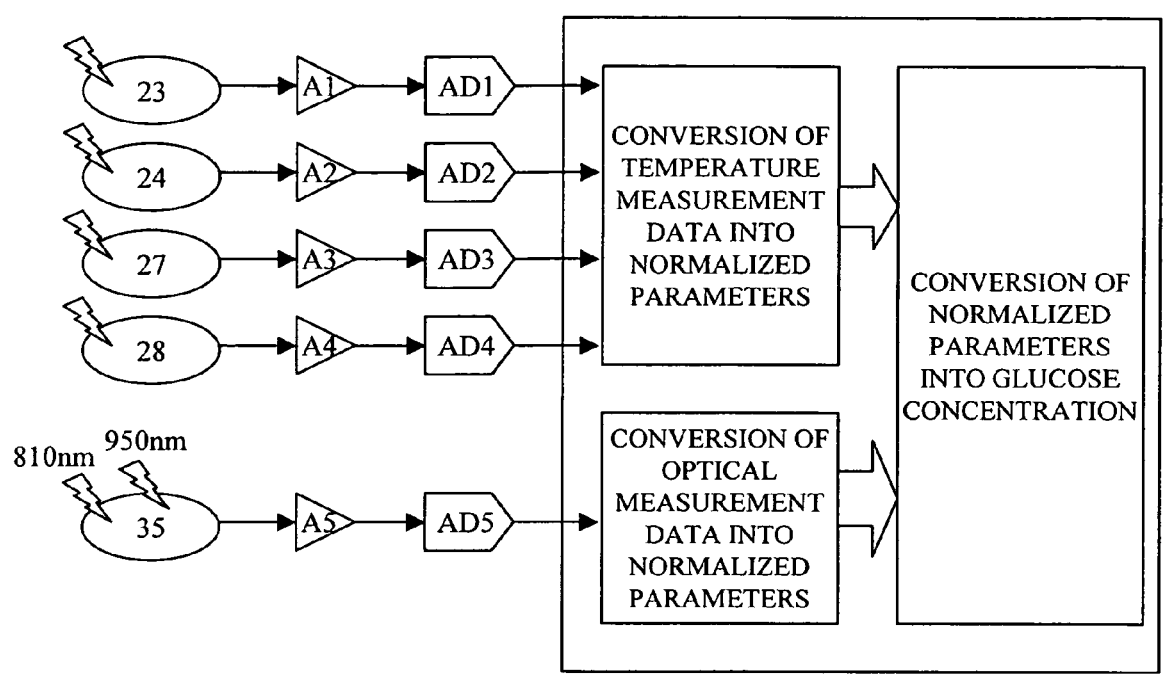
FIG. 8 is a conceptual chart illustrating the flow of data processing in the apparatus.

FIG. 8 is a conceptual chart illustrating the flow of data processing in the apparatus. The apparatus according to the present example is equipped with five sensors, namely thermistor 23, thermistor 24, pyroelectric detector 27, thermistor 28 and photodiode 35. The photodiode 35 measures the absorbance at wavelength 810 nm and the absorbance at wavelength 950 nm. Thus, six kinds of measurement values are fed to the apparatus.

Five kinds of analog signals are supplied via amplifiers A1 to A5 and digitally converted by analog/digital converters AD1 to AD5. Based on the digitally converted values, parameters $x_i$ (i=1, 2, 3, 4, 5) are calculated. The following are specific descriptions of $x_i$ (where $a_1$ to $a_5$ are proportionality coefficients):

Parameter proportional to heat radiation $$x_1 = a_1 \times (T_3)^4$$

Parameter proportional to heat convection $$x_2 = a_2 \times (T_4 - T_3)$$

Parameter proportional to hemoglobin concentration $$x_3 = a_3 \left(\frac{A_1}{a \times A_{HbO_2}(810 \text{ nm})}\right)$$

Parameter proportional to hemoglobin saturation $$x_4 = a_4 \times \left(\frac{A_2 \times A_{HbO_2}(810 \text{ nm}) - A_1 \times A_{Hb}(950 \text{ nm})}{A_1 \times (A_{HbO_2}(950 \text{ nm}) - A_{Hb}(950 \text{ nm}))}\right)$$

Parameter proportional to blood flow volume $$x_5 = a_5 \times \left(\frac{1}{t_{CONT} \times (S_1 - S_2)}\right)$$

Then, normalized parameters are calculated from mean values and standard deviations of parameters $x_i$ obtained from actual data from large numbers of able-bodied people and diabetic patients. A normalized parameter $X_i$ (where i=1, 2, 3, 4, 5) is calculated from each parameter $x_i$ according to the following equation:

$$X_i = \frac{x_i - \bar{x}_i}{SD(x_i)}$$

where
$x_i$: parameter
$\bar{x}_i$: mean value of the parameter
$SD(x_i)$: standard deviation of the parameter Calculations are conducted to convert the above five normalized parameters into a glucose concentration to be eventually displayed. Programs necessary for computations are stored in the ROM built inside the microprocessor in the apparatus. Memory areas necessary for computations are ensured in a RAM built inside the apparatus. The results of the calculations are displayed on the LCD portion.

The ROM stores, as a constituent element of the program necessary for the computations, a function for determining glucose concentration C in particular. The function is defined as follows. C is expressed by a below-indicated equation (1), where $a_i$ (i=0, 1, 2, 3, 4, 5) is determined from a plurality of pieces of measurement data in advance according to the following procedure:

(1) A multiple regression equation is created that indicates the relationship between the normalized parameter and the glucose concentration C.
(2) Normalized equations (simultaneous equations) relating to the normalized parameter are obtained from an equation obtained by the least-squares method.
(3) Values of coefficient $a_i$ (i=0, 1, 2, 3, 4, 5) are determined from the normalized equation and then substituted into the multiple regression equation.

Initially, the regression equation (1) indicating the relationship between the glucose concentration C and the normalized parameters $X_1$, $X_2$, $X_3$, $X_4$ and $X_5$ is formulated.

$$C = f(X_1, X_2, X_3, X_4, X_5) \quad (1)$$
$$= a_0 + a_1 X_1 + a_2 X_2 + a_3 X_3 + a_4 X_4 + a_5 X_5$$

Then, the least-squares method is employed to obtain a multiple regression equation that would minimize the error with respect to a measured value $C_i$ of glucose concentration according to an enzyme electrode method. When the sum of squares of the residual is D, D is expressed by the following equation (2):

$$D = \sum_{i=1}^{n} d_i^2 \quad (2)$$
$$= \sum_{i=1}^{n} (C_i - f(X_{i1}, X_{i2}, X_{i3}, X_{i4}, X_{i5}))^2$$
$$= \sum_{i=1}^{n} \{C_i - (a_0 + a_1 X_{i1} + a_2 X_{i2} + a_3 X_{i3} + a_4 X_{i4} + a_5 X_{i5})\}^2$$

The sum of squares of the residual D becomes minimum when partial differentiation of equation (2) with respect to $a_0, a_2, \ldots, a_5$ gives zero. Thus, we have the following equations:

$$\frac{\partial D}{\partial a_0} = -2\sum_{i=1}^{n} \{C_i - (a_0 + a_1 X_{i1} + a_2 X_{i2} + a_3 X_{i3} + a_4 X_{i4} + a_5 X_{i5})\} = 0 \quad (3)$$

$$\frac{\partial D}{\partial a_1} =$$
$$-2\sum_{i=1}^{n} X_{i1}\{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_2} =$$
$$-2\sum_{i=1}^{n} X_{i2}\{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_3} =$$
$$-2\sum_{i=1}^{n} X_{i3}\{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_4} =$$
$$-2\sum_{i=1}^{n} X_{i4}\{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_5} =$$
$$-2\sum_{i=1}^{n} X_{i5}\{C_i - (a_0 + a_1 X_{i1} + a_2 X_{i2} + a_3 X_{i3} + a_4 X_{i4} + a_5 X_{i5})\} = 0$$

When the mean values of C and $X_1$ to $X_5$ are $C_{mean}$ and $X_{1mean}$ to $X_{5mean}$, respectively, since $X_{imean}=0$ (i=1 to 5), equation (1) yields equation (4) thus:

$$a_0 = C_{mean} - a_1 X_{1mean} - a_2 X_{2mean} - a_3 X_{3mean} - a_4 X_{4mean} - a_5 X_{5mean} \quad (4)$$
$$= C_{mean}$$

The variation and covariation between the normalized parameters are expressed by equation (5). Covariation between the normalized parameter $X_i$ (i=1 to 5) and C is expressed by equation (6).

$$S_{ij} = \sum_{k=1}^{n} (X_{ki} - X_{imean})(X_{kj} - X_{jmean}) \quad (5)$$
$$= \sum_{k=1}^{n} X_{ki} X_{kj} \quad (i, j = 1, 2, \ldots 5)$$

$$S_{iC} = \sum_{k=1}^{n} (X_{ki} - X_{imean})(C_k - C_{mean}) \quad (6)$$
$$= \sum_{k=1}^{n} X_{ki}(C_k - C_{mean}) \quad (i = 1, 2, \ldots 5)$$

Substituting equations (4), (5), and (6) into equation (3) and rearranging yields simultaneous equations (normalized equations) (7). Solving equations (7) yields $a_1$ to $a_5$.

$$a_1 S_{11} + a_2 S_{12} + a_3 S_{13} + a_4 S_{14} + a_5 S_{15} = S_{1C}$$
$$a_1 S_{21} + a_2 S_{22} + a_3 S_{23} + a_4 S_{24} + a_5 S_{25} = S_{2C}$$
$$a_1 S_{31} + a_2 S_{32} + a_3 S_{33} + a_4 S_{34} + a_5 S_{35} = S_{3C}$$
$$a_1 S_{41} + a_2 S_{42} + a_3 S_{43} + a_4 S_{44} + a_5 S_{45} = S_{4C}$$
$$a_1 S_{51} + a_2 S_{52} + a_3 S_{53} + a_4 S_{54} + a_5 S_{55} = S_{5C} \quad (7)$$

Constant term $a_0$ is obtained by means of equation (4). The thus obtained $a_i$ (i=0, 1, 2, 3, 4, 5) is stored in ROM at the time of manufacture of the apparatus. In actual measurement using the apparatus, the normalized parameters $X_1$ to $X_5$ obtained from the measured values are substituted into regression equation (1) to calculate the glucose concentration C.

Hereafter, an example of the process of calculating the glucose concentration will be described. The coefficients in equation (1) are determined in advance based on a large quantity of data obtained from able-bodied persons and diabetic patients. The ROM in the microprocessor stores the following formula for the calculation of glucose concentration:

$$C = 99.4 + 18.3 \times X_1 - 20.2 \times X_2 - 23.7 \times X_3 - 22.0 \times X_4 - 25.9 \times X_5$$

$X_1$ to $X_5$ are the results of normalization of parameters $x_1$ to $x_5$. Assuming the distribution of the parameters is normal, 95% of the normalized parameters take on values between −2 and +2.

In an example of measured values for an able-bodied person, substituting normalized parameters $X_1 = -0.06$, $X_2 = +0.04$ and $X_3 = +0.05$, $X_4 = -0.12$ and $X_5 = +0.10$ in the above equation yields C=96 mg/dL. In an example of measured values for a diabetic patient, substituting normalized parameters $X_1 = +1.15$, $X_2 = -1.02$, $X_3 = -0.83$, $X_4 = -0.91$ and $X_5 = -1.24$ in the equation yields C=213 mg/dL.

Hereafter, the results of measurement by the conventional enzymatic electrode method and those by the embodiment of the invention will be described. In the enzymatic electrode method, a blood sample is reacted with a reagent and the amount of resultant electrons is measured to determine blood sugar level. When the glucose concentration was 89 mg/dL according to the enzymatic electrode method in an example of measured values for an able-bodied person, substituting normalized parameters $X_1 = -0.06$, $X_2 = +0.04$, $X_3 = +0.05$, $X_4 = -0.12$ and $X_5 = +0.10$ obtained by measurement at the same time according to the inventive method into the above equation yield C=96 mg/dL. Further, when the glucose concentration was 238 mg/dL according to the enzymatic electrode method in an example of measurement values for a diabetic patient, substituting $X_1 = +1.15$, $X_2 = -1.02$, $X_3 = -0.83$, $X_4 = -0.91$ and $X_5 = -1.24$ obtained by measurement at the same time according to the inventive method yields C=213 mg/dL. From the above results, it has been confirmed that the glucose concentration can be accurately determined using the method of the invention.

Figure 9:
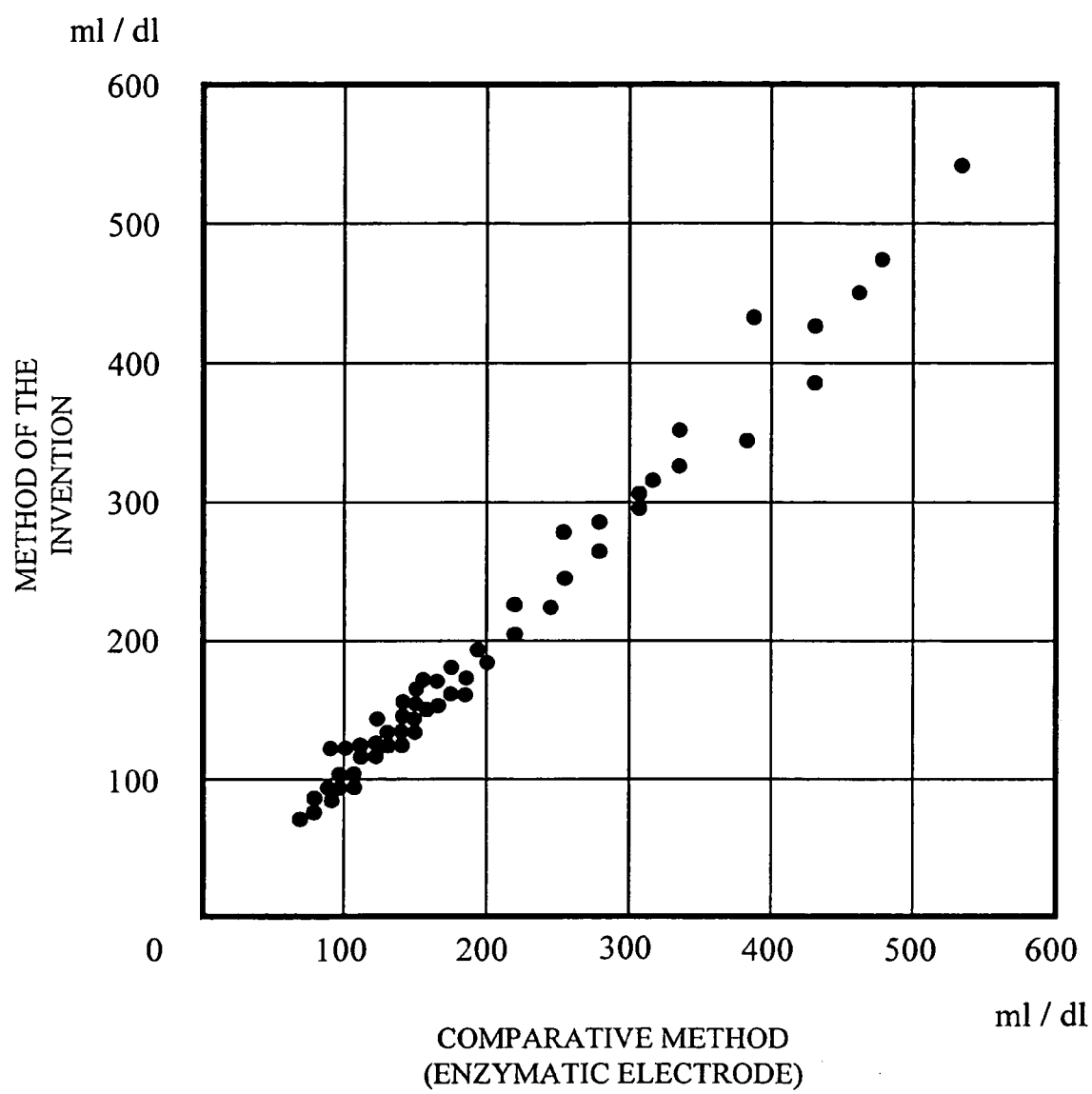
FIG. 9 shows the plots of the glucose concentration value calculated by the invention and the glucose concentration value measured by the enzyme electrode method.

FIG. 9 shows a chart plotting on the vertical axis the values of glucose concentration calculated by the inventive method and on the horizontal axis the values of glucose concentration measured by the enzymatic electrode method, based on measurement values obtained from a plurality of patients. A good correlation is obtained by measuring the oxygen supply volume and blood flow volume according to the invention (correlation coefficient=0.9324).

In the above-described embodiment, the parameters relating to blood hemoglobin concentration and blood hemoglobin oxygen saturation are obtained by spectroscopically measuring the hemoglobin in blood. However, the hemoglobin concentration is stable in persons without such symptoms as anemia, bleeding or erythrocytosis. The hemoglobin concentration is normally in the range between 13 to 18 g/dL for males and between 12 to 17 g/dL for females, and the range of variation of hemoglobin concentration from the normal values is 5 to 6%. Further, the weight of the term in the aforementioned formula for calculating blood sugar level is smaller than other terms. Therefore, the hemoglobin concentration can be treated as a constant without greatly lowering the measurement accuracy. Similarly, the hemoglobin oxygen saturation is stable between 97 to 98% if the person is undergoing aerial respiration at atmospheric pressure, at rest and in a relaxed state. Thus the hemoglobin concentration and the hemoglobin oxygen saturation can be treated as constants, and the oxygen supply volume can be determined from the product of the hemoglobin concentration constant, the hemoglobin oxygen saturation constant and the blood flow volume.

By treating the hemoglobin concentration and hemoglobin oxygen saturation as constants, the sensor arrangement for measuring blood sugar level can be simplified by removing the optical sensors, for example. Further, by eliminating the time necessary for optical measurement and the processing thereof, the procedure for blood sugar level measurement can be accomplished in less time.

Because the hemoglobin oxygen saturation takes on a stable value when at rest, in particular, by treating the hemoglobin concentration and hemoglobin oxygen saturation as constants, the measurement accuracy for blood sugar level measurement when at rest can be increased, and the procedure blood sugar level measurement can be accomplished in less time. By "when at rest" herein is meant the state in which the test subject has been either sitting on a chair or lying and thus moving little for approximately five minutes.

Hereafter, an embodiment will be described in which the blood hemoglobin concentration and blood hemoglobin oxygen saturation are treated as constants. This embodiment is similar to the above-described embodiment except that the blood hemoglobin concentration and blood hemoglobin oxygen saturation are treated as constants, and therefore the following description mainly concerns the differences from the earlier embodiment.

Figure 19A:
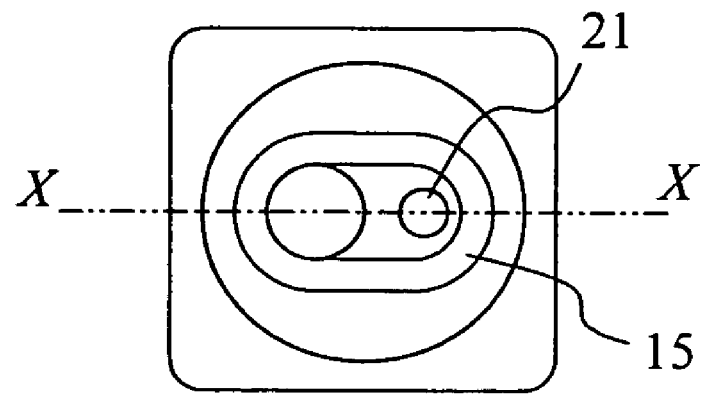
FIG. 19 shows the details of another example of the measurement portion.
Figure 19B:
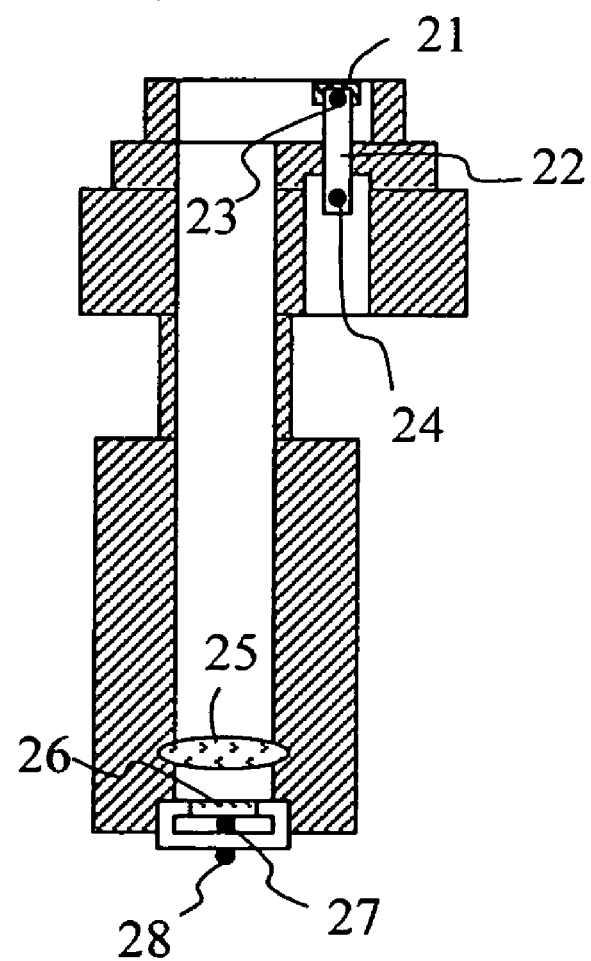

In the present embodiment, the hemoglobin concentration and hemoglobin oxygen saturation shown in FIG. 4 are not measured but treated as constants. Therefore, as shown in FIG. 19, the measurement portion of the present embodiment has the structure of the measurement portion of the earlier embodiment shown in FIG. 7 from which the light sources 33 and 34, photodiode 35 and optical fibers 31 and 32 are removed. Parameters used in the present embodiment are parameter $x_1$ proportional to heat radiation, parameter $x_2$ related to heat convection, and parameter $x_3$ proportional to the oxygen supply volume (hereafter, parameter proportional to oxygen supply volume will be indicated as $x_3$). From these parameters, normalized parameters are calculated in the manner described above, and a glucose concentration is calculated based on the three normalized parameters $X_i$ (i=1, 2, 3). During data processing, the step "CONVERSION OF OPTICAL MEASUREMENT DATA INTO NORMALIZED PARAMETERS" (see FIG. 8), which is necessary in the previous embodiment, can be omitted.

Figure 20:
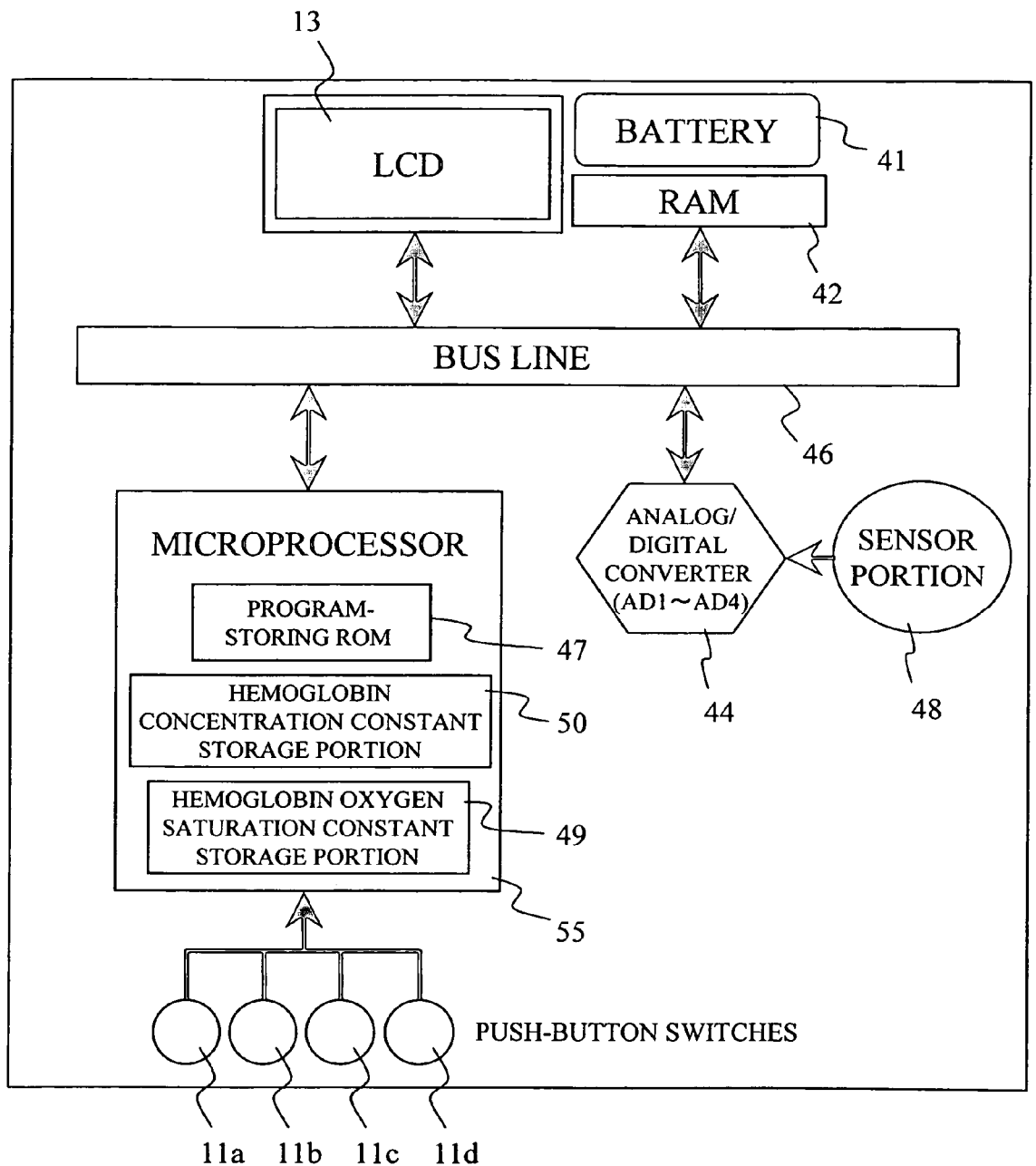
FIG. 20 is a conceptual chart illustrating the location where data is stored in the apparatus.

FIG. 20 shows a functional block diagram of the apparatus according to the embodiment. The apparatus runs on battery 41. A signal measured by sensor portion 48 including a temperature sensor is fed to analog/digital converters 44 (AD1 to AD4) provided for individual signals and is converted into a digital signal. Analog/digital converters AD1 to AD4, LCD 13 and RAM 42 are peripheral circuits for microprocessor 55. They are accessed by the microprocessor 55 via bus line 46. The push buttons 11a to 11d are connected to microprocessor 55. The microprocessor 55 includes the ROM for storing software. By pressing the buttons 11a to 11d, external instructions can be entered into microprocessor 55.

The ROM 47 included in the microprocessor 55 stores a program necessary for computations, i.e., it has the function of an arithmetic unit. The microprocessor 55 further includes a hemoglobin concentration constant storage portion 50 for storing hemoglobin concentration constants, and a hemoglobin oxygen saturation constant storage portion 49 for storing hemoglobin oxygen saturation constants. After the measurement of the finger is finished, the computing program calls optimum constants from the hemoglobin concentration storage portion 50 and hemoglobin oxygen saturation constant storage portion 49 and perform calculations. A memory area necessary for computations is ensured in the RAM 42 similarly incorporated into the apparatus. The result of computations is displayed on the LCD portion.

The ROM stores, as a constituent element of the program necessary for the computations, a function for determining glucose concentration C in particular. The function is defined as follows. C is expressed by a below-indicated equation (8), where $a_i$ (i=0, 1, 2, 3) is determined from a plurality of pieces of measurement data in advance according to the following procedure:

(1) A multiple regression equation is created that indicates the relationship between the normalized parameter and the glucose concentration C.
(2) Normalized equations (simultaneous equations) relating to the normalized parameter are obtained from an equation obtained by the least-squares method.
(3) Values of coefficient $a_i$ (i=0, 1, 2, 3) are determined from the normalized equation and then substituted into the multiple regression equation.

Initially, the regression equation (8) indicating the relationship between the glucose concentration C and the normalized parameters $X_1$, $X_2$ and $X_3$ is formulated.

$$C = f(X_1, X_2, X_3) \qquad (8)$$
$$= a_0 + a_1 X_1 + a_2 X_2 + a_3 X_3$$

Then, the least-squares method is employed to obtain a multiple regression equation that would minimize the error with respect to a measured value $C_i$ of glucose concentration according to an enzyme electrode method. When the sum of squares of the residual is D, D is expressed by the following equation (9):

$$D = \sum_{i=1}^{n} d_i^2 \qquad (9)$$
$$= \sum_{i=1}^{n} (C_i - f(X_{i1}, X_{i2}, X_{i3}))^2$$
$$= \sum_{i=1}^{n} \{C_i - (a_0 + a_1 X_{i1} + a_2 X_{i2} + a_3 X_{i3})\}^2$$

The sum of squares of the residual D becomes minimum when partial differentiation of equation (9) with respect to $a_0$ to $a_3$ gives zero. Thus, we have the following equations:

$$\frac{\partial D}{\partial a_0} = -2\sum_{i=1}^{n} \{C_i - (a_0 + a_1 X_{i1} + a_2 X_{i2} + a_3 X_{i3})\} = 0 \qquad (10)$$

$$\frac{\partial D}{\partial a_1} = -2\sum_{i=1}^{n} X_{i1}\{C_i - (a_0 + a_1 X_{i1} + a_2 X_{i2} + a_3 X_{i3})\} = 0$$

$$\frac{\partial D}{\partial a_2} = -2\sum_{i=1}^{n} X_{i2}\{C_i - (a_0 + a_1 X_{i1} + a_2 X_{i2} + a_3 X_{i3})\} = 0$$

$$\frac{\partial D}{\partial a_3} = -2\sum_{i=1}^{n} X_{i3}\{C_i - (a_0 + a_1 X_{i1} + a_2 X_{i2} + a_3 X_{i3})\} = 0$$

When the mean values of C and $X_1$ to $X_3$ are $C_{mean}$ and $X_{1mean}$ to $X_{3mean}$, respectively, since $X_{imean}=0$ (i=1 to 3), equation (8) yields equation (11) thus:

$$a_0 = C_{mean} - a_1 X_{1mean} - a_2 X_2 mean - a_3 X_3 mean \qquad (11)$$
$$= C_{mean}$$

The variation and covariation between the normalized parameters are expressed by equation (12). Covariation between the normalized parameter $X_i$ (i=1 to 3) and C is expressed by equation (13).

$$S_{ij} = \sum_{k=1}^{n} (X_{ki} - X_{imean})(X_{kj} - X_{jmean}) \qquad (12)$$
$$= \sum_{k=1}^{n} X_{ki} X_{kj} \quad (i, j = 1, 2, 3)$$

$$S_{iC} = \sum_{k=1}^{n} (X_{ki} - X_{imean})(C_k - C_{mean}) \qquad (13)$$
$$= \sum_{k=1}^{n} X_{ki}(C_k - C_{mean}) \quad (i = 1, 2, 3)$$

Substituting equations (11), (12), and (13) into equation (10) and rearranging yields simultaneous equations (normalized equations) (14). Solving equations (14) yields $a_1$ to $a_3$.

$$a_1 S_{11} + a_2 S_{12} + a_3 S_{13} = S_{1C}$$
$$a_1 S_{21} + a_2 S_{22} + a_3 S_{23} = S_{2C}$$
$$a_1 S_{31} + a_2 S_{32} + a_3 S_{33} = S_{3C} \qquad (14)$$

Constant term $a_0$ is obtained by means of equation (11). The thus obtained $a_i$ (i=0, 1, 2, 3) is stored in ROM at the time of manufacture of the apparatus. In actual measurement using the apparatus, the normalized parameters $X_1$ to $X_3$ obtained from the measured values are substituted into regression equation (8) to calculate the glucose concentration C.

Hereafter, an example of the process of calculating the glucose concentration will be described. The coefficients in equation (8) are determined in advance based on a large quantity of data obtained from able-bodied persons and diabetic patients. The ROM in the microprocessor stores the following formula for the calculation of glucose concentration:

$$C = 101.7 + 25.8 \times X_1 - 23.2 \times X_2 - 12.9 \times X_3$$

$X_1$ to $X_3$ are the results of normalization of parameters $x_1$ to $x_3$. Assuming the distribution of the parameters is normal, 95% of the normalized parameters take on values between −2 and +2.

In an example of measured values for an able-bodied person, substituting normalized parameters $X_1=-0.06$, $X_2=+0.04$ and $X_3=+0.10$ in the above equation yields C=101 mg/dL. In an example of measured values for a diabetic patient, substituting normalized parameters $X_1=+1.35$, $X_2=-1.22$ and $X_3=-1.24$ in the equation yields C=181 mg/dL. In the above equation, the hemoglobin concentration and hemoglobin oxygen saturation are rendered into constants of 15 g/dL and 97%, respectively.

Hereafter, the results of measurement by the conventional enzymatic electrode method and those by the embodiment of the invention will be described. In the enzymatic electrode method, a blood sample is reacted with a reagent and the amount of resultant electrons is measured to determine glucose concentration. When the glucose concentration was 93 mg/dL according to the enzymatic electrode method in an example of measured values for an able-bodied person, substituting normalized parameters $X_1=-0.06$, $X_2=+0.04$ and $X_3=+0.10$ obtained by measurement at the same time according to the inventive method into the above equation yielded C=101 mg/dL. Further, when the glucose concentration was 208 mg/dL according to the enzymatic electrode method in an example of measurement values for a diabetic patient, substituting $X_1=+1.35$, $X_2=-1.22$ and $X_3=-1.24$ obtained by measurement at the same time according to the inventive method yielded C=181 mg/dL. Although the calculation results indicate an error of about 13%, this level of accuracy is considered sufficient because normally errors between 15% and 20% are considered acceptable in blood sugar level measuring apparatuses in general. Thus, it has been confirmed that the method of the invention can allow glucose concentrations to be determined with high accuracy.

Figure 21:
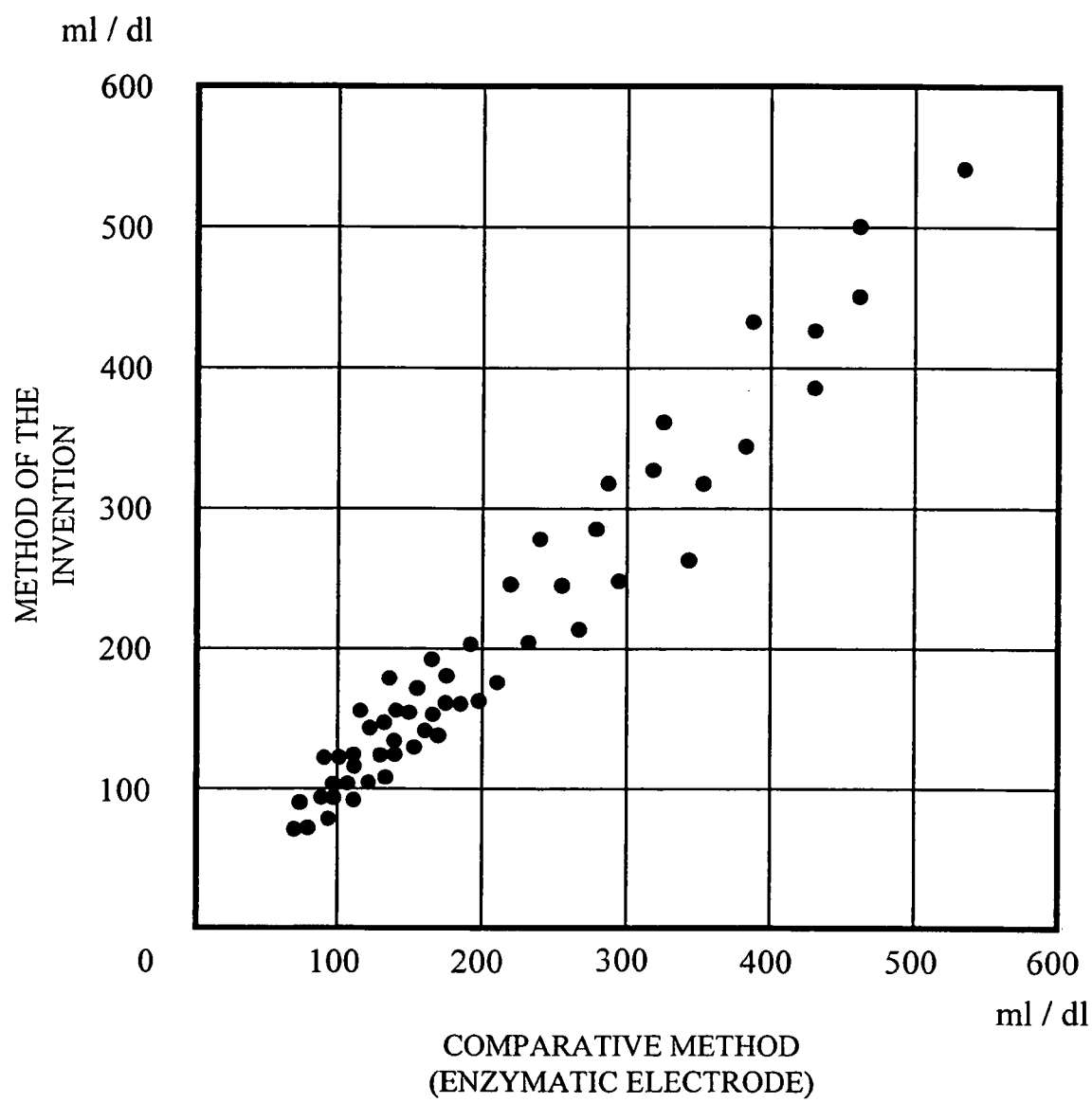
FIG. 21 shows the plots of the glucose concentration value calculated by the invention and the glucose concentration value measured by the enzyme electrode method.

FIG. 21 shows a chart plotting on the vertical axis the values of glucose concentration calculated by the inventive method and on the horizontal axis the values of glucose concentration measured by the enzymatic electrode method, based on measurement values obtained from a plurality of patients. A good correlation is obtained by measuring according to the invention (correlation coefficient=0.8932).

What is claimed is:

1. A blood sugar level measuring apparatus comprising:
   a heat amount measurement portion for measuring a plurality of temperatures derived from a body surface and obtaining information used for calculating the amount of heat transferred by convection and the amount of heat transferred by radiation, both related to the dissipation of heat from said body surface;
   an oxygen level measuring portion for obtaining information about blood oxygen level;
   a storage portion for storing a relationship between parameters corresponding to said plurality of temperatures and blood oxygen level and blood sugar levels;
   a calculating portion which converts a plurality of measurement values fed from said heat amount measuring portion and said oxygen level measurement portion into said parameters, and computes a blood sugar level by applying said parameters to said relationship stored in said storage portion;
   a display portion for displaying the blood sugar level calculated by said calculating portion; and
   a warning control portion, wherein:
   said oxygen level measurement portion includes a blood flow volume measurement portion for obtaining information about blood flow volume, and an optical measurement portion for obtaining hemoglobin concentration and hemoglobin oxygen saturation in blood, wherein said blood flow volume measurement portion includes:
   a body-surface contact portion;
   an adjacent temperature detector disposed adjacent to said body-surface contact portion;
   an indirect temperature detector for detecting the temperature at a position spaced apart from said body-surface contact portion; and
   a heat conducting member connecting said body-surface contact portion and said indirect temperature detector, and wherein:
   said warning control portion causes said display portion to display a warning if the blood sugar level calculated by said calculating portion is larger than a warning blood sugar level.

2. The blood sugar level measuring apparatus according to claim 1, wherein said warning value includes a warning value for a fasting blood sugar level and a warning value for nonfasting blood sugar level.

3. The blood sugar level measuring apparatus according to claim 2, wherein said warning value is a fixed value.

4. The blood sugar level measuring apparatus according to claim 2, wherein said warning value is variable.

5. A blood sugar level measuring apparatus comprising:
   an ambient temperature measuring device for measuring ambient temperature;
   a body-surface contact portion to which a body surface is brought into contact;
   a radiant heat detector for measuring radiant heat from said body surface;
   a heat conducting member disposed in contact with said body-surface contact portion;
   an adjacent temperature detector disposed adjacent to said body-surface contact portion; an indirect temperature detector disposed at a position that is adjacent to said heat conducting member and that is spaced apart from said body-surface contact portion, said indirect temperature detector measuring temperature at the position spaced apart from said body-surface contact portion;
   a light source for irradiating said body-surface contact portion light with at least two different wavelengths;
   a light detector for detecting reflected light produced as said light is reflected by said body surface;
   a converter for converting outputs from said adjacent temperature detector, said indirect temperature detector, said ambient temperature detector, said radiant temperature detector and said light detector, into parameters;
   a calculating portion in which a relationship between said parameters and blood sugar levels is stored in advance, and which calculates a blood sugar level by applying said parameters to said relationship;
   a display for displaying the blood sugar level outputted from said calculating portion; and
   a warning control portion, wherein:
   said warning control portion causes said display portion to display a warning if the blood sugar level calculated by said calculating portion is larger than a warning blood sugar level.

6. The blood sugar level measuring apparatus according to claim 5, wherein said warning value includes a warning value for fasting blood sugar level and a warning value for nonfasting blood sugar level.

7. The blood sugar level measuring apparatus according to claim 5, wherein said warning value is a fixed value.

8. The blood sugar level measuring apparatus according to claim 5, wherein said warning value is variable.

9. A blood sugar level measuring apparatus comprising:
   an ambient temperature measuring device for measuring ambient temperature;
   a body-surface contact portion to which a body surface is brought into contact;

a radiant heat detector for measuring radiant heat from said body surface;

a heat conducting member disposed in contact with said body-surface contact portion;

an adjacent temperature detector disposed adjacent to said body-surface contact portion;

an indirect temperature detector disposed at a position that is adjacent to said heat conducting member and that is spaced apart from said body-surface contact portion, said indirect temperature detector measuring temperature at the position spaced apart from said body-surface contact portion;

a storage portion where information about blood hemoglobin concentration and blood hemoglobin oxygen saturation is stored;

a converter for converting outputs from said adjacent temperature detector, said indirect temperature detector, said ambient temperature measuring device and said radiant heat detector, into a plurality of parameters;

a calculating portion in which relationships among said parameters, said information about blood hemoglobin concentration and blood hemoglobin oxygen saturation and blood sugar levels are stored, said calculating portion including a processing portion for calculating a blood sugar level by applying at least said parameters to said relationships;

a display for displaying the blood sugar level outputted from said calculating portion; and a warning control portion, wherein:

said warning control portion causes said display portion to display a warning if the blood sugar level calculated by said calculating portion is larger than a warning blood sugar level.

10. The blood sugar level measuring apparatus according to claim 9, wherein said processing portion calculates said blood sugar level by applying said parameters and optimum constants for blood hemoglobin concentration and blood hemoglobin oxygen saturation from said storage portion to said relationships.

* * * * *